(12) United States Patent
Dellinger et al.

(10) Patent No.: US 7,135,565 B2
(45) Date of Patent: Nov. 14, 2006

(54) SYNTHESIS OF POLYNUCLEOTIDES USING COMBINED OXIDATION/DEPROTECTION CHEMISTRY

(75) Inventors: Douglas J. Dellinger, Sunnyvale, CA (US); Michael G. M. Perbost, Bethany, CT (US); Marvin H. Caruthers, Boulder, CO (US); Jason R. Betley, Suffolk (GB)

(73) Assignees: Agilent Technologies, Inc., Palo Alto, CA (US); University of Colorado, Boulder, CO (US)

(*) Notice: Subject to any disclaimer, the term of this patent is extended or adjusted under 35 U.S.C. 154(b) by 60 days.

(21) Appl. No.: 09/916,369

(22) Filed: Jul. 27, 2001

(65) Prior Publication Data

US 2002/0058802 A1 May 16, 2002

Related U.S. Application Data

(63) Continuation-in-part of application No. 09/627,249, filed on Jul. 28, 2000, now abandoned.

(51) Int. Cl.
*C07H 21/00* (2006.01)
*C07H 21/02* (2006.01)
*C07H 21/04* (2006.01)

(52) U.S. Cl. .............. 536/25.3; 536/22.1; 536/23.1; 536/24.3; 536/25.31; 536/25.33; 536/25.34; 435/6

(58) Field of Classification Search ............. 536/25.3, 536/22.1, 23.1, 24.3, 25.31, 25.33, 25.34; 435/6
See application file for complete search history.

(56) References Cited

U.S. PATENT DOCUMENTS

| | | |
|---|---|---|
| 4,415,732 A | 11/1983 | Caruthers et al. |
| 4,458,066 A | 7/1984 | Caruthers et al. |
| 4,500,707 A | 2/1985 | Caruthers et al. |
| 4,668,777 A | 5/1987 | Caruthers et al. |
| 4,725,677 A | 2/1988 | Koster et al. |
| 4,808,708 A | 2/1989 | Yoshida et al. |
| 4,973,679 A | 11/1990 | Caruthers et al. |
| 5,132,418 A | 7/1992 | Caruthers et al. |
| 34,069 A | 9/1992 | Koster et al. |
| 5,210,264 A | 5/1993 | Yau |
| 5,705,621 A | 1/1998 | Ravikumar |
| 5,763,599 A | 6/1998 | Pfleiderer et al. |
| 5,861,242 A | 1/1999 | Chee et al. |
| 5,874,554 A | 2/1999 | Gamble et al. |
| 5,908,926 A | 6/1999 | Pirrung et al. |
| 6,008,400 A | 12/1999 | Scaringe et al. |
| 6,069,243 A | 5/2000 | Scozzari |
| 6,147,205 A | 11/2000 | McGall et al. |
| 6,166,198 A | 12/2000 | Livingston |
| 6,207,819 B1 * | 3/2001 | Manoharan et al. ....... 536/25.3 |
| 6,222,030 B1 * | 4/2001 | Dellinger et al. .......... 536/25.3 |
| 6,376,246 B1 * | 4/2002 | Crameri et al. ............ 435/440 |
| 2002/0045221 A1 | 4/2002 | Dellinger et al. |
| 2002/0055880 A1 | 5/2002 | Unold et al. |
| 2003/0129589 A1 | 7/2003 | Koster et al. |

FOREIGN PATENT DOCUMENTS

| | | |
|---|---|---|
| EP | 0 241 363 A1 | 4/1987 |
| EP | 0 742 287 A2 | 9/1996 |
| EP | 0 984 021 A2 | 3/1999 |
| EP | 0 984 021 A3 | 3/1999 |
| EP | 0 428 810 A2 | 7/1999 |
| EP | 1 428 810 A2 | 7/1999 |
| WO | WO 92/10092 | 11/1991 |
| WO | WO 96/28457 | 3/1996 |
| WO | WO98/41531 | 1/1998 |
| WO | WO 98/41531 | 3/1998 |
| WO | WO 99/54509 | 4/1998 |
| WO | WO 98/393348 | 5/1998 |
| WO | WO 00/27859 | 6/1998 |
| WO | WO 00/18778 | 9/1999 |
| WO | WO 00/61594 | 4/2000 |

OTHER PUBLICATIONS

Y. Hayakawa, M. Uchiyama and R. Nyori, "Nonaqueous Oxidation of Nucleoside Phosphites to the Phosphates", Chemical Center and Department of Chemistry, Nagoya University, Tetrahedron Letters, vol. 27, No. 35, pp. 4191–4194, 1986.

Serge L. Beaucaga and Redhakrishnam P. Iyer, "Advances in the Synthesis of Oligonucleotides by the Phosphoramidite Approach", Tetrahedron Report No. 9, vol. 48, No. 12, pp. 2223–2311, 1992; Administration, Bethesada, Maryland 20892.

Jean–Louis Fourrey and Jeanette Varenne, "Introduction of a Nonaqueous Oxidation Procedures in the Phosphite Triester Route for Oligonucleotide Synthesis", Tetrahedron Letters, vol. 6, No. 9, pp. 1217–1220, 1985.

European Search Report, Dec. 21, 2002, pp. 26–27.

Herald Sigmund, Thomas Maier and Wolfgang Pfleidner, "A New Type of Fluoresecene Labeling of Nucleosides, Nucleotides and Oligonucleotides", Nucleosides & Nucleotides, 16(5&6) pp. 685–696 (1997).

(Continued)

*Primary Examiner*—Samuel Barts
*Assistant Examiner*—Patrick Lewis
(74) *Attorney, Agent, or Firm*—Michael J. Beck

(57) ABSTRACT

A method of synthesizing a polynucleotide which can, for example, be used during fabrication of an array. A second nucleoside is coupled to a first nucleoside through a phosphite linkage, with the second nucleoside having a hydroxyl protecting group that is a non-carbonate protecting group. The product of the foregoing step is exposed to a composition which both oxidizes the formed phosphite to a phosphate and deprotects the protected hydroxyl of the coupled nucleoside. The method has particular application to fabricating an addressable array of polynucleotides on a substrate which carries substrate bound moieties each with a hydroxyl group.

11 Claims, 4 Drawing Sheets

OTHER PUBLICATIONS

Ahmad Hasan, Hong Li, Jeno Tomasz and Barbara Ramsey Shaw, "Base–boronated dinucleotides: synthesis and effect of N7–cyanoborane substitution on the base protons", Nucleic Acids Research, 1996, vol. 24, No. 11, pp. 2150–2157.

Frank Bergman, and Wolfgang Pfleidner, The 2–Dansylethoxycarbonyl (==2–{5–(Dimethylamino) naphtixalen–1–y1}sulfonyl{ethoxycarbonyl;Dnseoc)Group for Protection of the 5'–Hydroxy Function in Oligodeoxyribonucleotide Synthesis', Helvetica Chimica Acta –vol. 77 (1994), pp. 203–214.

Michael C. Pirrung and Lora Fallon, Proofing of Photolithographic DNA Synthesis with 3', 5'Dimethoxybenzoinyloxycarbonyl–Protected Deoxynucleoside Phosphoramidites', American Chemical Society, 1998, pp. 241–246.

Frank Bergman, Erich Kueng, Patric Iaiza, and Willi Bannwarth, "Allyl as Intemucleotide Protecting Group in DNA Synthesis to be Cleaved Off by Ammonia", Tetrahedron, vol. 51, No. 25, pp. 6974–6976.

Mitsuo Sekine, Narihiro Masuda and Tsujiaki Hata, "Synthesis of Oligodeoxyribonucleotides Involving a Rapid Procedure for Removal of Base–Protecting Groups by Use of the 4.4'–Tris(benzoyloxy)trityl (TBTr) Group", The Chemical Society of Japan, 59, pp. 1781–1789, Jun. 1986.

Reiko Iwase, Mitsuo Sekine, Tsujaki Hata and Kin–ichiro Miura, "A New Method for the Synthesis of Capped Oligoribonucleotides by Use of an Appropriately Protected 7–Methylguanosine Diphosphate Derivative as a Donor for the Triphosphate Bond Formation", Tetrahedron Letters, vol. 29, No. 24, pp. 2969–2972, 1988.

J. Katzhendler, S. Cohen, E. Rahamin, M. Weisz, I. Ringel and J. Deutsch, The Effect of Spacer, Linkage and Solid Support on the Synthesis of Oilgonucleotides', Tetrahedron, vol. 45, No. 9, pp. 2777–2792, 1989.

David W. Will, Gerhard Breiphol, Dietrich Langner, Jochen Knolle and Eugene Uhlmann, The Synthesis of Polyamide Nucleic Acids Using a Novel Monoethoxyrithl Protecting–Group Society', Terahedron, vol. 51, No. 44, pp. 12069–12082, 1995.

Takashi Kamimura, Masahiko Tsuchiya, Ken–ichi Urakami, Koji Koura, Mitsuo Sekine, Kazuko Shinozaki, Kin–ichiro Miura, and Tsuujiaki Hata, "Synthesis of a Dodecaribonucleotide, GUAUCAAUAAUG By Use of Fully" Protected Rinonucleotide Building Blocks', American Chemical Society, 1984, pp. 4552–4557.

Mitsuo Sekine and Tsujiaki Hata, "Synthesis of Short Oligoribonucleotides Bearing a 3'–or 5'–Terminal Phosphate by Use of 4.4', 4"–Tris(4,5–dichlorophthalimido)trityl as a New 5'–Hydroxyl Protecting Group", American Chemical Society, 1986, pp. 4581–4586.

Mitsuo Sekine, Narihiro Masuda and Tsujiaki Hata, "Introduction of the 4, 4'4""–Tris(Benzoyloxy)Trityl Group into the Exo Amino Groups of Deoxyribonucleotides and its Properties', Tetrahedron, vol. 41, No. 23 pp. 5445–5453.

A. Nyilas, C. Glemarec & J. Chattopadhyaya, Synthesis of [3'(O)>5'(C)]–Oxyacetamido Linked Nucleotide Tetrahedron, vol. 46, No. 6, pp. 2149–2164, 1990.

Yoshihiro Hayakawa, "Regiodefined Synthesis and Conformational Properties of Adenyldiyl Trimers with Unsymmetrical 2'–5'and 3' –5'Intermucleotide Linkages", Tetrahedron, vol. 51, No. 36, pp. 9899–9916, 1995.

H. Koster, "Polymer Support Oligonucleotide Synthesis VI 1–5 Use of Inorganic Carriers", Tetrahedron Letters, No. 16, pp. 1527–1530, 1972.

U.S. Appl. No. 09/128,052, filed Aug. 3, 1998, Douglas J. Dellinger, et al.

Michael C. Pirrung and Jean–Claude Bradley, "Comparison Methods for Photochemical Phosphoramidite –Based DNA Synthesis", J. Org. Chem. 1995, 60 pp. 6270–6276. Department of Chemistry, P. M. Gross Chemical Laboratory, Duke University, Durnham, North Carolina 27708–0346.

Hayes Dougan, John B. HObbs, Jeffrey I. Witz and Donald m. Lyster, "Syntesis and Radiodination of a Stannyl Oligodeoxyribonucleotide", Nucleic Acids Research, 1997, vol. 25, No. 14, pp. 2897–2901.

Shigenori Iwai and Eiko Ohtsuka, "5'–Levulinyl and 2'–tetrahydrofuranyl protection for the synthesis of Oligoribonucleotides by the phosphoramidite approach", Nucleic Acids Research, vol. 6, No. 20, 1988, pp. 9443–9456.

* cited by examiner

◯ = Solid support/growing oligonucleotide

◯ = Solid support/growing oligonucleotide

SEQUENCE LISTING

<160> NUMBER OF SEQ ID NOS: 9

<210> SEQ ID NO 1
<211> LENGTH: 20
<212> TYPE: DNA
<213> ORGANISM: artificial sequence
<220> FEATURE:
<223> OTHER INFORMATION: synthetic sequence

<400> SEQUENCE: 1
tttttttttt tttttttttt                                          20

<210> SEQ ID NO 2
<211> LENGTH: 20
<212> TYPE: DNA
<213> ORGANISM: artificial sequence
<220> FEATURE:
<223> OTHER INFORMATION: synthetic sequence

<400> SEQUENCE: 2
tccccccccc cccccccccc                                          20

<210> SEQ ID NO 3
<211> LENGTH: 20
<212> TYPE: DNA
<213> ORGANISM: artificial sequence
<220> FEATURE:
<223> OTHER INFORMATION: synthetic sequence

<400> SEQUENCE: 3
taaaaaaaaa aaaaaaaaaa                                          20

<210> SEQ ID NO 4
<211> LENGTH: 20
<212> TYPE: DNA
<213> ORGANISM: artificial sequence
<220> FEATURE:
<223> OTHER INFORMATION: synthetic sequence

<400> SEQUENCE: 4
tgtgtgtgtg tgtgtgtgtg                                          20

<210> SEQ ID NO 5
<211> LENGTH: 26
<212> TYPE: DNA
<213> ORGANISM: artificial sequence
<220> FEATURE:
<223> OTHER INFORMATION: synthetic sequence

<400> SEQUENCE: 5
tatcatcgta gctggtcagt gtatcc                                   26

<210> SEQ ID NO 6
<211> LENGTH: 25
<212> TYPE: DNA
<213> ORGANISM: artificial sequence
<220> FEATURE:
<223> OTHER INFORMATION: synthetic sequence

<400> SEQUENCE: 6
tgaggtggta tctagtgagg ggaca                                    25

<210> SEQ ID NO 7
<211> LENGTH: 10

```
<212> TYPE: DNA
<213> ORGANISM: artificial sequence
<220> FEATURE:
<223> OTHER INFORMATION: synthetic sequence

<400> SEQUENCE: 7
ttttttttt                                                          10

<210> SEQ ID NO 8
<211> LENGTH: 10
<212> TYPE: DNA
<213> ORGANISM: artificial sequence
<220> FEATURE:
<223> OTHER INFORMATION: synthetic sequence

<400> SEQUENCE: 8
tgtgtgtgtg                                                         10

<210> SEQ ID NO 9
<211> LENGTH: 20
<212> TYPE: DNA
<213> ORGANISM: artificial sequence
<220> FEATURE:
<223> OTHER INFORMATION: synthetic sequence

<400> SEQUENCE: 9
tttttttttt cccccccccc                                              20
```

SYNTHESIS OF POLYNUCLEOTIDES USING COMBINED OXIDATION/DEPROTECTION CHEMISTRY

RELATED APPLICATIONS

This application is a continuation-in-part of copending U.S. patent application Ser. No. 09/627,249 filed on Jul. 28, 2000, now abandoned entitled "Polynucleotide Synthesis Useful In Array Fabrication", the entire contents of which are incorporated herein by reference. Related subject matter is disclosed in U.S. Pat. No. 6,222,030 to Dellinger et al. (Apr. 24, 2001).

FIELD OF THE INVENTION

The invention relates generally to chemical synthesis of polynucleotides. The invention more specifically relates the synthesis of polynucleotides by performing a single combined oxidation and deprotection step.

BACKGROUND OF THE INVENTION

Conventional phosphoramidite chemistry, so named for a functional group on the monomer building blocks, was first developed in the early 1980's as disclosed in U.S. Pat. No. 4,415,732. This functional group provided a relatively efficient means of joining a building block monomer to the growing chain. Solid phase synthesis disclosed by Caruthers et al. in U.S. Pat. No. 4,458,066 was another improvement to oligonucleotide synthesis. In this technique, the growing DNA chain is attached to an insoluble support via a long organic linker which allows the growing DNA chain to be solubilized in the solvent in which the support is placed. The solubilized, yet immobilized, DNA chain is thereby allowed to react with reagents in the surrounding solvent and allows for the easy washing away of the reagents from the solid support to which the oligonucleotide is attached. These significant advances in phosphoramidite chemistry and solid phase synthesis paved the way to making custom DNA synthesis accessible to the average biology lab. Other novel techniques, e.g. polymerase chain reaction ("PCR", which is used in forensic testing and DNA fingerprinting), have been facilitated due to the ready availability of synthetic DNA.

There are several sites on the nucleosides of similar chemical nature, e.g.——OH or hydroxyl groups. However, during oligonucleotide synthesis, the monomer subunits must be attached to the growing oligonucleotide molecule in a site-specific manner. This requires functionalizing a site either on the growing chain or on the incoming base for attachment of the incoming monomer building block to the growing chain. To prevent the incoming monomer from attaching at the wrong site, the wrong sites must be blocked while the correct site is left open to react. This requires the use of what are termed protecting groups. Protecting groups are compounds attached temporarily to a potentially reactive site so as to prevent it from reacting. The protecting group must be stable during said reactions and yet must eventually be removed to yield the original site. The synthesis of oligonucleotides requires several sites to be protected and particular sites must be deprotected while others remain protected. These protecting groups grouped together as a set are termed orthogonal protecting groups.

Solid phase oligonucleotide synthesis protocols typically use a dimethoxytrityl protecting group for the 5' hydroxyl of nucleosides. A phosphoramidite functionality is utilized at the 3' hydroxyl position. The synthesis generally proceeds from the 3' to the 5' of the ribose or deoxyribose sugar component of the phosphoramidite nucleoside in a synthesis cycle which adds one nucleotide at a time to the growing oligonucleotide chain. Beaucage et al. (1981) *Tetrahedron Lett.* 22:1859. See FIG. 1 for a schematic representation of this technology. In FIG. 1 "B" represents a purine or pyrimidine base, "DMT" represents dimethoxytrityl protecting group and "iPr" represents isopropyl. In the first step of the synthesis cycle, the "coupling" step, the 5' end of the growing chain is coupled with the 3' phosphoramidite of the incoming monomer to form a phosphite triester intermediate (the 5' hydroxyl of the added monomer has a protecting group so only one new monomer is added to the growing chain per cycle). Matteucci et al. (1981) *J. Am. Chem. Soc.* 103:3185. Next, an optional "capping reaction" is used to stop the synthesis on any chains having an unreacted 5' hydroxyl, which would be one nucleotide short at the end of synthesis. The phosphite triester intermediate is subjected to oxidation (the "oxidation" step) after each coupling reaction to yield a more stable phosphotriester intermediate. Without oxidation, the unstable phosphite triester linkage would cleave under the acidic conditions of subsequent synthesis steps. Letsinger et al. (1976) *J. Am. Chem. Soc.* 98:3655. Removal of the 5' protecting group of the newly added monomer (the "deprotection" step) is typically accomplished by reaction with acidic solution to yield a free 5' hydroxyl group, which can be coupled to the next protected nucleoside phosphoramidite. This process is repeated for each monomer added until the desired sequence is synthesized.

According to some protocols, the synthesis cycle of couple, cap, oxidize, and deprotect is shortened by omitting the capping step or by taking the oxidation step 'outside' of the cycle and performing a single oxidation reaction on the completed chain. For example, oligonucleotide synthesis according to H-phosphonate protocols will permit a single oxidation step at the conclusion of the synthesis cycles. However, coupling yields are less efficient than those for phosphoramidite chemistry and oxidation requires longer times and harsher reagents than amidite chemistry.

The chemical group conventionally used for the protection of nucleoside 5'-hydroxyls is dimethoxytrityl ("DMT"), which is removable with acid. Khorana (1968) *Pure Appl. Chem.* 17:349; Smith et al. (1962) *J. Am. Chem. Soc.* 84:430. This acid-labile protecting group provides a number of advantages for working with both nucleosides and oligonucleotides. For example, the DMT group can be introduced onto a nucleoside regioselectively and in high yield. Brown et al. (1979) *Methods in Enzymol.* 68:109. Also, the lipophilicity of the DMT group greatly increases the solubility of nucleosides in organic solvents, and the carbocation resulting from acidic deprotection gives a strong chromophore, which can be used to indirectly monitor coupling efficiency. Matteucci et al. (1980) *Tetrahedron Lett.* 21:719. In addition, the hydrophobicity of the group can be used to aid separation on reverse-phase HPLC. Becker et al. (1985) *J. Chromatogr.* 326:219.

However, use of DMT as a hydroxyl-protecting group in oligonucleotide synthesis is also problematic. The N-glycosidic linkages of oligodeoxyribonucleotides are susceptible to acid catalyzed cleavage (Kochetkov et al., *Organic Chemistry of Nucleic Acids* (New York: Plenum Press, 1972)), and even when the protocol is optimized, recurrent removal of the DMT group with acid during oligonucleotide synthesis results in depurination. Shaller et al. (1963) *J. Am. Chem. Soc.* 85:3821. The N-6-benzoyl-protected deoxyadenosine nucleotide is especially susceptible to glycosidic cleavage, resulting in a substantially reduced yield of the final oligonucleotide. Efcavitch et al. (1985) *Nucleosides & Nucleotides* 4:267. Attempts have been made to address the problem of acid-catalyzed depurination utilizing alternative mixtures of acids and various solvents; see, for example, Sonveaux (1986) *Bioorganic Chem.* 14:274. However, this approach has met with limited success. McBride et al. (1986) *J. Am. Chem. Soc.* 108:2040.

Conventional synthesis of oligonucleotides using DMT as a protecting group is problematic in other ways as well. For example, cleavage of the DMT group under acidic conditions gives rise to the resonance-stabilized and long-lived bis(p-anisyl)phenylmethyl carbocation. Gilham et al. (1959) *J. Am. Chem. Soc.* 81:4647. Protection and deprotection of hydroxyl groups with DMT are thus readily reversible reactions, resulting in side reactions during oligonucleotide synthesis and a lower yield than might otherwise be obtained. To circumvent such problems, large excesses of acid are used with DMT to achieve quantitative deprotection. As bed volume of the polymer is increased in larger scale synthesis, increasingly greater quantities of acid are required. The acid-catalyzed depurination which occurs during the synthesis of oligodeoxyribonucleotides is thus increased by the scale of synthesis. Caruthers et al, in *Genetic Engineering: Principles and Methods*, J. K. Setlow et al., Eds. (New York: Plenum Press, 1982).

Considerable effort has been directed to developing 5'-O-protecting groups which can be removed under non-acidic conditions. For example, Letsinger et al. (1967) *J. Am. Chem. Soc.* 89:7147, describe use of a hydrazine-labile benzoyl-propionyl group, and deRooij et al. (1979) *Real. Track. Chain. Pays-Bas.* 98:537, describe using the hydrazine-labile levulinyl ester for 5'-OH protection (see also Iwai et al. (1988) *Tetrahedron Lett.* 29:5383; and Iwai et al. (1988) *Nucleic Acids Res.* 16:9443). However, the cross-reactivity of hydrazine with pyrimidine nucleotides (as described in Baron et al. (1955) *J. Chem. Soc.* 2855 and in Habermann (1962) *Biochem. Biophys. Acta* 55:999), the poor selectivity of levulinic anhydride and hydrazine cleavage of N-acyl protecting groups (Letsinger et al. (1968), *Tetrahedron Lett.* 22:2621) have made these approaches impractical. Seliger et al. (1985), *Nucleosides & Nucleotides* 4:153, describes the 5'-O-phenyl-azophenyl carbonyl ("PAPco") group, which is removed by a two-step procedure involving transesterification followed by β-elimination; however, unexpectedly low and non-reproducible yields resulted. Fukuda et al. (1988) *Nucleic Acids Res. Symposium Ser.* 19, 13, and Lehmann et al. (1989) *Nucleic Acids Res.* 17:2389, describe application of the 9-fluorenylmethylcarbonate ("Fmoc") group for 5'-protection. Lehmann et al. (1989) report reasonable yields for the synthesis of oligonucleotides up to 20 nucleotides in length. The basic conditions required for complete deprotection of the Fmoc group, however, lead to problems with protecting group compatibility. Similarly, Letsinger et al. (1967), *J. Am. Chem. Soc.* 32:296, describe using the p-nitrophenyloxycarbonyl group for 5'-hydroxyl protection. In all of the procedures described above utilizing base-labile 5'-O-protecting groups, the requirements of high basicity and long deprotection times have severely limited their application for routine synthesis of oligonucleotides.

Still an additional drawback associated with conventional oligonucleotide synthesis using DMT as a hydroxyl-protecting group is the necessity of multiple steps, particularly the post-synthetic deprotection step in which the DMT group is removed following oxidation of the internucleoside phosphite triester linkage to a phosphorotriester. It would be desirable to have a synthesis protocol where the hydroxyl-protecting group could be removed concurrently with oxidation, such that the final two steps involved in nucleotide addition, namely oxidation and deprotection, could be combined.

The problems associated with the use of DMT are exacerbated in solid phase oligonucleotide synthesis where "microscale" parallel reactions are taking place on a very dense, packed surface. Applications in the field of genomics and high throughput screening have fueled the demand for precise chemistry in such a context. Thus, increasingly stringent demands are placed on the chemical synthesis cycle as it was originally conceived, and the problems associated with conventional methods for synthesizing oligonucleotides are rising to unacceptable levels in these expanded applications.

Our own previous research on using carbonate protecting groups resulted in the discovery that carbonate groups could be used with good effect to reduce depurination during the synthesis and to combine the oxidation step with the removal of the carbonate protecting group. U.S. Pat. No. 6,222,030 to Dellinger et al. (Apr. 24, 2001).

Oligonucleotides may be useful as diagnostic or screening tools, for example, on polynucleotide arrays. Such arrays include regions of usually different sequence polynucleotides arranged in a predetermined configuration on a substrate. These regions (sometimes referenced as "features") are positioned at respective locations ("addresses") on the substrate. The arrays, when exposed to a sample, will exhibit an observed binding pattern. This binding pattern can be detected upon interrogating the array. For example all polynucleotide targets (for example, DNA) in the sample can be labeled with a suitable label (such as a fluorescent compound), and the fluorescence pattern on the array accurately observed following exposure to the sample. Assuming that the different sequence polynucleotides were correctly deposited in accordance with the predetermined configuration, then the observed binding pattern will be indicative of the presence and/or concentration of one or more polynucleotide components of the sample.

Polynucleotide arrays can be fabricated by depositing previously obtained polynucleotides onto a substrate, or by in situ synthesis methods. The in situ fabrication methods include those described in WO 98/41531 and the references cited therein. The in situ method for fabricating a polynucleotide array typically follows, at each of the multiple different addresses at which features are to be formed, the same conventional iterative sequence used in forming polynucleotides on a support by means of known chemistry.

The foregoing methods of preparing polynucleotides are well known and described in detail, for example, in Caruthers (1985) *Science* 230: 281–285; Itakura et al., *Ann. Rev. Biochem.* 53: 323–356; Hunkapillar et al. (1984) *Nature* 310: 105–110; and in "Synthesis of Oligonucleotide Derivatives in Design and Targeted Reaction of Oligonucleotide Derivatives", CRC Press, Boca Raton, Fla., pages 100 et seq.; U.S. Pat. No. 4,458,066; U.S. Pat. No. 4,500,707; U.S. Pat. No. 5,153,319; U.S. Pat. No. 5,869,643; EP 0294196, and elsewhere. The phosphoramidite and phosphite triester approaches are most broadly used, but other approaches include the phosphodiester approach, the phosphotriester approach and the H-phosphonate approach.

In the case of array fabrication, different monomers may be deposited at different addresses on the substrate during any one iteration so that the different features of the completed array will have different desired polynucleotide sequences. One or more intermediate further steps may be required in each iteration, such as the conventional oxidation and washing steps.

Each iteration of the foregoing conventional sequence can have a very high yield (over 90%), with each step being relatively rapid (requiring less than a minute). Thus, the foregoing conventional sequence is ideal for preparing a particular polynucleotide on a packed column. Whether the preparation requires four or five minutes is usually not great concern. However, when it is desired to mass produce a polynucleotide array with hundreds or more typically, thousands, of features each carrying different polynucleotides requiring ten, twenty or more cycles, the time taken for each step in each cycle at each feature becomes much more important. Furthermore, each step in the cycle requires its own solutions and appropriate system of delivery to the substrate during in situ array fabrication, which complicates an in situ array fabrication apparatus and can lead to more waste. It would be desirable then, to provide a means of fabricating an array by the in situ process with a simplified synthesis cycle requiring requiring fewer steps and/or less time to complete each cycle. It would further be desirable if the number of solutions required for each cycle could be reduced.

SUMMARY

The invention is thus addressed to the aforementioned deficiencies in the art, and provides a novel method for synthesizing oligonucleotides, wherein the method has numerous advantages relative to prior methods such as those discussed above.

The present invention in its broadest sense encompasses materials and methods for use in site-specific step-wise synthesis that yield polymer chains, e.g., as in the formation of oligonucleotides. The synthesis protocol begins with the preparation of a first chain including at least one monomer. This preparation step preferably includes attaching the substituted monomer to an insoluble support. The substituted monomer is deprotected if necessary to expose a reactive site. A second protected monomer having one or more hydroxyl protecting groups is reacted with the deprotected reactive site of the chain to yield an elongated chain. An optional capping step may be included in the synthesis cycle, if desired. The elongated chain is then subjected to a combined oxidation/deprotection step which allows the oxidation and deprotection reactions to occur concurrently in the same reaction solution. That is, the oxidation of the backbone of the elongated chain and the deprotection of the reactive site in the elongated chain occur at substantially the same time upon application of a single combined oxidation/deprotection reagent composition to the elongated chain. The deprotection of the reactive site on the elongated chain allows the cycle to repeat with the addition of the third substituted monomer. The synthesis cycle disclosed above is repeated until the desired chain length is achieved.

The method provides for concurrent oxidation of the internucleoside linkage and removal of the hydroxyl protecting group, eliminating the extra step present in conventional processes for synthesizing oligonucleotides. In addition, the method can be used in connection with fluorescent or other readily detectable protecting groups, enabling monitoring of individual reaction steps. Further, the method is useful in carrying out either 3'-to-5' synthesis or 5'-to-3' synthesis. Finally, because of the far more precise chemistry enabled by the present invention, the method readily lends itself to the highly parallel, microscale synthesis of oligonucleotides.

It is an object of the invention to provide a composition that is a single combined oxidation/deprotection reagent solution that may be added to the elongated chain during the synthesis cycle to bring about the concurrent oxidation of the internucleoside linkage and deprotection of the reactive site hydroxyl.

It is a further object of the invention to provide reagents and methods for synthesis of oligonucleotides allowing the synthesis to be conducted under a wide range of conditions and allowing for the use of a variety of protecting groups. The reagents and methods described are particularly useful for fabricating an addressable array of polynucleotides on a substrate. In this case, at each of the multiple different addresses on the substrate (for example, at least one hundred, at least one thousand, or at least ten thousand addresses), the synthesis cycle is repeated so as to form the addressable array with different polynucleotide sequences at different addresses. In the array forming method, the nucleosides to be coupled at respective addresses are deposited as droplets at those addresses. Preferably, all of the substrate may be simultaneously exposed to the combined oxidation/deprotection reagent.

Additional objects, advantages, and novel features of this invention shall be set forth in part in the descriptions and examples that follow and in part will become apparent to those skilled in the art upon examination of the following specifications or may be learned by the practice of the invention. The objects and advantages of the invention may be realized and attained by means of the instruments, combinations, compositions and methods particularly pointed out in the appended claims.

BRIEF DESCRIPTION OF THE FIGURES

Embodiments of the invention will now be described with reference to the drawings, in which.

To facilitate understanding, identical reference numerals have been used, where practical, to designate identical elements that are common to the figures.

DETAILED DESCRIPTION

Figure 1:
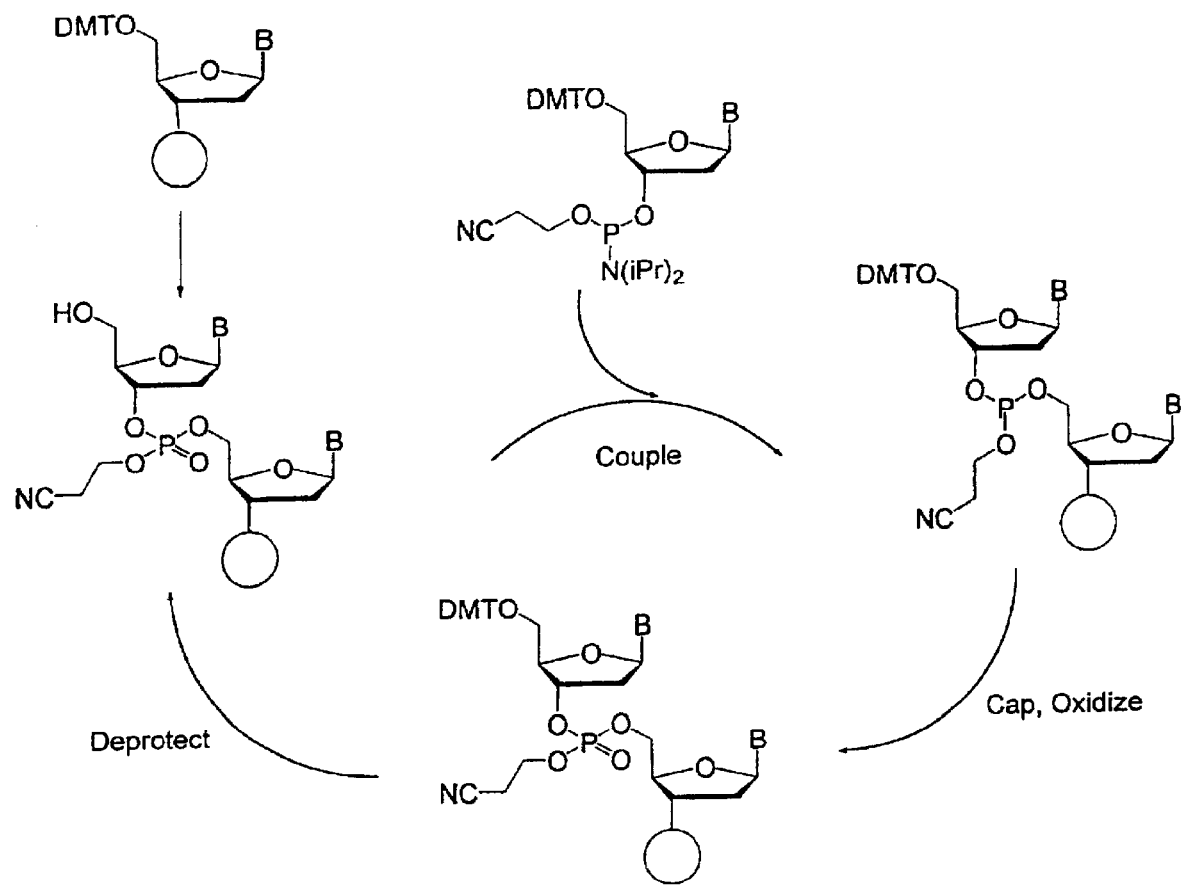
FIG. 1 schematically illustrates a prior art oligonucleotide synthesis method using phosphoramidite monomers. The figure shows separate oxidation and deprotection steps are necessary.

Before the invention is described in detail, it is to be understood that unless otherwise indicated this invention is not limited to particular materials, reagents, reaction materials, manufacturing processes, or the like, as such may vary. It is also to be understood that the terminology used herein is for purposes of describing particular embodiments only, and is not intended to be limiting. It is also possible in the present invention that steps may be executed in different sequence where this is logically possible. However, the sequence described below is preferred.

It must be noted that, as used in the specification and the appended claims, the singular forms "a," "an" and "the" include plural referents unless the context clearly dictates otherwise. Thus, for example, reference to "a mass analyzer" includes a plurality of mass analyzers. In this specification and in the claims that follow, reference will be made to a number of terms that shall be defined to have the following meanings unless a contrary intention is apparent:

As used herein, polynucleotides include single or multiple stranded configurations, where one or more of the strands may or may not be completely aligned with another. The terms "polynucleotide" and "oligonucleotide" shall be generic to polydeoxynucleotides (containing 2-deoxy-D-ribose), to polyribonucleotides (containing D-ribose), to any other type of polynucleotide which is an N-glycoside of a purine or pyrimidine base, and to other polymers in which the conventional backbone has been replaced with a non-naturally occurring or synthetic backbone or in which one or more of the conventional bases has been replaced with a synthetic base, providing that the polymers contain nucleobases in a configuration which allows for base pairing and base stacking, such as is found in DNA and RNA.

A "nucleotide" refers to a sub-unit of a nucleic acid (whether DNA or RNA) which includes a phosphate group, a 5 carbon sugar and a nitrogen containing base, as well as analogs of such sub-units. A "nucleoside" references the same sub-unit but without a phosphate group. An "oligonucleotide" generally refers to a nucleotide multimer of about 5 to 100 nucleotides in length, while a "polynucleotide" includes a nucleotide multimer having any number of nucleotides. It will be appreciated that, as used herein, the terms "nucleoside" and "nucleotide" will include those moieties which contain not only the naturally occurring purine and pyrimidine bases (A, G, T, C, or U), but also modified purine and pyrimidine bases and other heterocyclic bases which have been modified (these moieties are sometimes referred to herein, collectively, as "purine and pyrimidine bases and analogs thereof"). Such modifications include methylated purines or pyrimidines, acylated purines or pyrimidines, and the like.

An "array", unless a contrary intention appears, includes any one, two or three dimensional arrangement of addressable regions bearing a particular chemical moiety or moieties (for example, biopolymers such as polynucleotide sequences) associated with that region. An array is "addressable" in that it has multiple regions of different moieties (for example, different polynucleotide sequences) such that a region (a "feature" or "spot" of the array) at a particular predetermined location (an "address") on the array will detect a particular target or class of targets (although a feature may incidentally detect non-targets of that feature). In the case of an array, the "target" will be referenced as a moiety in a mobile phase (typically fluid), to be detected by probes ("target probes") which are bound to the substrate at the various regions. However, either of the "target" or "target probes" may be the one which is to be evaluated by the other (thus, either one could be an unknown mixture of polynucleotides to be evaluated by binding with the other). While probes and targets of the present invention will typically be single-stranded, this is not essential. An "array layout" refers to one or more characteristics of the array, such as feature positioning, feature size, and some indication of a moiety at a given location. "Hybridizing" and "binding", with respect to polynucleotides, are used interchangeably.

A "protecting group" is used in the conventional chemical sense to reference a group which reversibly renders unreactive a functional group under specified conditions of a desired reaction. After the desired reaction, protecting groups may be removed to deprotect the protected functional group. All protecting groups should be removable (and hence, labile) under conditions which do not degrade a substantial proportion of the polynucleotides being synthesized. In contrast to a protecting group, a "capping group" permanently binds to a segment of a molecule to prevent any further chemical transformation of that segment. A "non-carbonate protecting group" is a protecting group used to protect a hydroxyl on a polynucleotide, nucleoside monomer, or nucleotide monomer, where the protecting group is attached to the protected polynucleotide, nucleoside monomer, or nucleotide monomer by other than a carbonate linkage. Examples of non-carbonate protecting groups are, for example, 3'- or 5'-O-silyl or -siloxyl protecting groups, 3'- or 5'-O-ester protecting groups, 3'- or 5'-O-carbamate protecting groups, and 3'- or 5'-O-triphenylmethyl protecting groups. A "hydroxyl protecting group" refers to a protecting group, especially a non-carbonate protecting group, where the protected group is a hydroxyl. A "reactive-site hydroxyl" is the terminal 5'-hydroxyl during 3'-5' polynucleotide synthesis and is the 3'-hydroxyl during 5'-3' polynucleotide synthesis. An "acid labile protected hydroxyl" is a hydroxyl group protected by a protecting group that can be removed by acidic conditions. Similarly, an "acid labile protecting group" is a protecting group that can be removed by acidic conditions.

A "group" includes both substituted and unsubstituted forms. Typical substituents include one or more lower alkyl, any halogen, hydroxy, or aryl. Any substituents are typically chosen so as not to substantially adversely affect reaction yield (for example, not lower it by more than 20% (or 10%, or 5% or 1%) of the yield otherwise obtained without a particular substituent or substituent combination). An "acetic acid" includes substituted acetic acids such as di-chloroacetic acid (DCA) or tri-chloroacetic acid (TCA).

A "phospho" group includes a phosphodiester, phosphotriester, and H-phosphonate groups. In the case of either a phospho or phosphite group, a moiety other than a substituted 5-membered furyl ring may be attached to O of the phospho or phosphite group which links between the furyl ring and the P atom.

The term "alkyl" as used herein, unless otherwise specified, refers to a saturated straight chain, branched or cyclic hydrocarbon group of 1 to 24, typically 1–12, carbon atoms, such as methyl, ethyl, n-propyl, isopropyl, n-butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. The term "lower alkyl" intends an alkyl group of one to eight carbon atoms, and includes, for example, methyl, ethyl, n-propyl, isopropyl, n-butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. The term "cycloalkyl" refers to cyclic alkyl groups such as cyclopropyl, cyclobutyl, cyclopentyl, cyclohexyl, cycloheptyl and cyclooctyl.

The term "alkenyl" as used herein, unless otherwise specified, refers to a branched, unbranched or cyclic (in the case of C5 and C6) hydrocarbon group of 2 to 24, typically 2 to 12, carbon atoms containing at least one double bond, such as ethenyl, vinyl, allyl, octenyl, decenyl, and the like. The term "lower alkenyl" intends an alkenyl group of two to eight carbon atoms, and specifically includes vinyl and allyl. The term "cycloalkenyl" refers to cyclic alkenyl groups.

The term "alkynyl" as used herein, unless otherwise specified, refers to a branched or unbranched hydrocarbon group of 2 to 24, typically 2 to 12, carbon atoms containing at least one triple bond, such as acetylenyl, ethynyl, n-propynyl, isopropynyl, n-butynyl, isobutynyl, t-butynyl, octynyl, decynyl and the like. The term "lower alkynyl" intends an alkynyl group of two to eight carbon atoms, and includes, for example, acetylenyl and propynyl, and the term "cycloalkynyl" refers to cyclic alkynyl groups.

The term "aryl" as used herein refers to an aromatic species containing 1 to 5 aromatic rings, either fused or linked, and either unsubstituted or substituted with 1 or more substituents typically selected from the group consisting of amino, halogen and lower alkyl. Preferred aryl substituents contain 1 to 3 fused aromatic rings, and particularly preferred aryl substituents contain 1 aromatic ring or 2 fused aromatic rings. Aromatic groups herein may or may not be heterocyclic. The term "aralkyl" intends a moiety containing both alkyl and aryl species, typically containing less than about 24 carbon atoms, and more typically less than about 12 carbon atoms in the alkyl segment of the moiety, and typically containing 1 to 5 aromatic rings. The term "aralkyl" will usually be used to refer to aryl-substituted alkyl groups. The term "aralkylene" will be used in a similar manner to refer to moieties containing both alkylene and aryl species, typically containing less than about 24 carbon atoms in the alkylene portion and 1 to 5 aromatic rings in the aryl portion, and typically aryl-substituted alkylene. Exemplary aralkyl groups have the structure —(CH2)j-Ar wherein j is an integer in the range of 1 to 24, more typically 1 to 6, and Ar is a monocyclic aryl moiety.

The term "electron withdrawing" denotes the tendency of a substituent to attract valence electrons of the molecule of which it is a part, i.e., an electron-withdrawing substituent is electronegative.

The term "alpha effect," as in an "alpha effect" nucleophilic deprotection reagent, is used to refer to an enhancement of nucleophilicity that is found when the atom adjacent a nucleophilic site bears a lone pair of electrons. As the term is used herein, a nucleophile is said to exhibit an "alpha effect" if it displays a positive deviation from a BrØnsted-type nucleophilicity plot. Hoz et al. (1985) *Israel J. Chem.* 26:313. See also, Aubort et al. (1970) *Chem. Comm.* 1378; Brown et al. (1979) *J. Chem. Soc. Chem. Comm.* 171; Buncel et al.(1982) *J. Am. Chem. Soc.* 104:4896; Edwards et al. (1962) *J. Amer. Chem. Soc.* 84:16; Evanseck et al. (1987) *J. Am. Chem Soc.* 109:2349. The magnitude of the alpha effect is dependent upon the electrophile which is paired with the specific nucleophile. McIsaac, Jr. et al. (1972), *J. Org. Chem.* 37:1037. Peroxy anions are example of nucleophiles which exhibit strong alpha effects.

The term "heterocyclic" refers to a five- or six-membered monocyclic structure or to an eight- to eleven-membered bicyclic structure which is either saturated or unsaturated. The heterocyclic groups herein may be aliphatic or aromatic. Each heterocycle consists of carbon atoms and from one to four heteroatoms selected from the group consisting of nitrogen, oxygen and sulfur. As used herein, the terms "nitrogen heteroatoms" and "sulfur heteroatoms" include any oxidized form of nitrogen and sulfur, and the quaternized form of any basic nitrogen. Examples of heterocyclic groups include piperidinyl, morpholinyl and pyrrolidinyl.

The term "halo" or "halogen" is used in its conventional sense to refer to a chloro, bromo, fluoro or iodo substituent.

It will also be appreciated that throughout the present application, words such as "upper", "lower" are used in a relative sense only. "Fluid" is used herein to reference a liquid.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present, and, thus, the description includes structures wherein a non-hydrogen substituent is present and structures wherein a non-hydrogen substituent is not present.

Oligonucleotide Synthesis Using Non-Carbonate Protecting Groups

In a first embodiment, the invention pertains to a method for synthesizing an oligonucleotide on a solid support, wherein a non-carbonate protecting group is used as a hydroxyl-protecting group. The novel synthesis is based on a simple, two-step cycle of (1) coupling a hydroxyl-protected nucleoside monomer to a growing oligonucleotide chain, and (2) applying a reagent solution that both removes the protecting group and oxidizes the internucleoside linkage to give a phosphotriester bond. The two step cycle of coupling and deprotection/oxidation steps are repeated as necessary to give an oligonucleotide having a desired sequence and length.

In the initial step of the synthesis, an initial nucleoside is covalently attached to a solid support to serve as the starting point for oligonucleotide synthesis. The initial nucleoside may be bound to the support through its 3'-hydroxyl group or its 5'-hydroxyl group, but is typically bound through the 3'-hydroxyl group. A second nucleoside monomer is then coupled to the free hydroxyl group of the support-bound initial nucleoside, wherein for 3'-to-5' oligonucleotide synthesis, the second nucleoside monomer has a phosphorus derivative such as a phosphoramidite at the 3' position and a non-carbonate protecting group at the 5' position, and alternatively, for 5'-to-3' oligonucleotide synthesis, the second nucleoside monomer has a phosphorus derivative at the 5' position and a non-carbonate protecting group at the 3' position. This coupling reaction gives rise to a newly formed internucleoside linkage between the initial nucleoside and the added nucleoside monomer, with the hydroxyl protecting group intact. In the second step of the synthesis, the non-carbonate protecting group is removed with a combined oxidation/deprotection reagent solution that also serves to oxidize the internucleoside linkage from a phosphite triester to the desired phosphotriester.

More specifically, for 3'-to-5' synthesis, a support-bound nucleoside monomer is provided having the structure (I)

wherein:
◯ represents the solid support or a support-bound oligonucleotide chain;
R is hydrido or hydroxyl (or hydroxy protecting group), wherein when R is hydrido, the support-bound nucleoside is a deoxyribonucleoside, as will be present in DNA synthesis, and when R is hydroxyl (or hydroxy protecting group), the support-bound nucleoside is a ribonucleoside, as will be present in RNA synthesis; and B is a purine or pyrimidine base. The purine or pyrimidine base may be conventional, e.g., adenine (A), thymine (T), cytosine (C), guanine (G) or uracil (U), or a protected form thereof, e.g., wherein the base is protected with a protecting group such as acetyl, difluoroacetyl, trifluoroacetyl, isobutyryl, benzoyl, or the like. The purine or pyrimidine base may also be an analog of the foregoing; suitable analogs will be known to those skilled in the art and are described in the pertinent texts and literature. Common analogs include, but are not limited to, 1-methyladenine, 2-methyladenine, N6-methyladenine, N6-isopentyladenine, 2-methylthio-N6-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)uracil, 5-(methylaminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine and 2,6-diaminopurine.

The protected monomer to be added has the structure of formula (II)

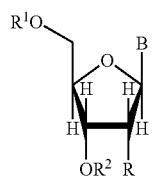

(II)

in which B and R are as defined above with respect to the support-bound nucleoside of structural formula (I), and R1 is a non-carbonate protecting group. The group R1 must be compatible with (that is, removable under) conditions which result in oxidation of the internucleoside linkage and which do not result in any significant amount of cleavage of the internucleoside linkage. This is satisfied by one of two conditions: 1) the phosphite triester is not cleaved under the conditions of protecting group removal, or 2) the rate of oxidation of the internucleoside linkage is significantly faster than the rate of cleavage of the internucleoside linkage. R1 may be, for example, a protecting group which is labile under nucleophilic attack under neutral or mildly basic conditions, or R1 may be a protecting group that is labile under acidic conditions. Suitable protecting groups for R1 are described in "Protective Groups in Organic Synthesis" by T. W. Green, Wiley Interscience. Preferred protecting groups which are labile under nucleophilic attack under neutral or mildly basic conditions are: ester protecting groups, carbamate protecting groups, siloxane protecting groups, silane protecting groups, and sulfonate protecting groups that β-eliminate. Other preferred protecting groups are functionalized trityl groups and levulinyloxy groups. Particularly preferred examples of non-carbonate protecting groups are, for example, 3'- or 5'-O-silyl or -siloxyl protecting groups, 3'- or 5'-O-ester protecting groups, 3'- or 5'-O-carbamate protecting groups, and 3'- or 5'-O-triphenylmethyl protecting groups.

Preferred protecting groups that are capable of removal under acidic conditions ("acid-labile protecting groups") include those such as tetrahydropyranyl groups, e.g. tetrahydropyran-2-yl and 4-methoxytetrahydropyran-2-yl; an arylmethyl group with n aryl groups (where n=1 to 3) and 3-n alkyl groups such as an optionally substituted trityl group, for example a monomethoxytrityl for oligoribonucleotide synthesis and a dimethoxytrityl for oligodeoxyribonucleotide synthesis, pixyl; isobutyloxycarbonyl; t-butyl; and dimethylsilyl. A trityl group is a triphenylmethyl group.

Particularly useful phosphoramidites, their preparation, and their use are described in detail in U.S. Pat. No. 5,902,878; U.S. Pat. No. 5,700,919; U.S. Pat. No. 4,668,777; U.S. Pat. No. 4,415,732; PCT publication WO 98/41531 and the references cited therein, among others. Removal of hydroxyl protecting groups from such nucleoside monomer moieties during polynucleotide synthesis is known.

Particularly useful protecting groups at the R1 position may incorporate a fluorescent or colored moiety. Preferably, in this embodiment, R1 experiences a fluorescence shift or color shift upon cleavage of the protecting group from the active site hydroxyl, but is neither fluorescent nor colored when bound to the active site hydroxyl. In this way, when the protecting group R1 is removed, the reaction may be monitored by detecting a fluorescent or colored cleavage product. Examples of fluorescent and colorimetric species that may be employed include, but are not limited to: xanthenes such as fluoresceins, eosins and erythrosins, with preferred fluorescein compounds exemplified by 6-carboxyfluorescein, 5- and 6-carboxy-4,7-dichlorofluorescein, 2',7'-dimethoxy-5- and 6-carboxy-4,7-dichlorofluorescein, 2',7'-dimethoxy-4',5'-dichloro-5- and 6-carboxyfluorescein, 2',7'-dimethoxy-4',5'-dichloro-5- and 6-carboxy-4,7-dichlorofluorescein, 1',2',7',8'-dibenzo-5- and 6-carboxy-4,7-dichlorofluorescein, 2',7'-dichloro-5- and 6-carboxy-4,7-dichlorofluorescein, and 2',4',5',7'-tetrachloro-5- and 6-carboxy-4,7-dichlorofluorescein; rhodamines such as tetramethylrhodamine and Texas Red®; benzimidazoles; ethidiums; propidiums; anthracyclines; mithramycins; acridines; actinomycins; merocyanines; coumarins such as 4-methyl-7-methoxycoumarin; pyrenes; chrysenes; stilbenes; anthracenes; naphthalenes such as dansyl, 5-dimethylamino-1-naphthalenesulfonyl; salicylic acids; benz-2-oxa-1-diazoles (also known as benzofurans), including 4-amino-7-nitrobenz-2-oxa-1,3-diazole; fluorescamine; and 4-methylumbelliferone.

Referring still to structure (II), R2 is a phosphorus derivative that enables coupling to a free hydroxyl group. R2 has the structure (III)

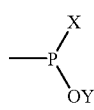

(III)

wherein X may be a halogen (particularly Cl or Br) or a secondary amino group, NQ1Q2. Preferred phosphorus derivatives are phosphoramidites, where X is NQ1Q2, and in which Q1 and Q2 may be the same or different and are typically selected from the group consisting of alkyl, aryl, aralkyl, alkaryl, cycloalkyl, alkenyl, cycloalkenyl, alkynyl, cycloalkynyl, optionally containing one or more nonhydrocarbyl linkages such as ether linkages, thioether linkages, oxo linkages, amine and imine linkages, and optionally substituted on one or more available carbon atoms with a nonhydrocarbyl substituent such as cyano, nitro, halo, or the like. Preferably, Q1 and Q2 represent lower alkyl, more preferably sterically hindered lower alkyls such as isopropyl, t-butyl, isobutyl, sec-butyl, neopentyl, tert-pentyl, isopentyl, sec-pentyl, and the like. Most preferably, Q1 and Q2 both represent isopropyl. Alternatively, Q1 and Q2 may be linked to form a mono- or polyheterocyclic ring having a total of from 1 to 3, usually 1 to 2 heteroatoms and from 1 to 3 rings. In such a case, Q1 and Q2 together with the nitrogen atom to which they are attached represent, for example, pyrrolidone, morpholino or piperidino. Usually, Q1 and Q2 have a total of from 2 to 12 carbon atoms. Examples of specific -NQ1 Q2 moieties thus include, but are not limited to, dimethylamine, diethylamine, diisopropylamine, dibutylamine, methylpropylamine, methylhexylamine, methylcyclopropylamine, ethylcyclohexylamine, methylbenzylamine, methylcyclohexylmethylamine, butylcyclohexylamine, morpholine, thiomorpholine, pyrrolidine, piperidine, 2,6-dimethylpiperidine, piperazine, and the like.

The moiety "Y" is hydrido or hydrocarbyl, typically alkyl, alkenyl, aryl, aralkyl, or cycloalkyl. Preferably, Y represents: lower alkyl; electron-withdrawing β-substituted aliphatic, particularly electron-withdrawing β-substituted ethyl such as β-trihalomethyl ethyl, β-cyanoethyl, β-sulfoethyl, β-nitro-substituted ethyl, and the like; electron-withdrawing substituted phenyl, particularly halo-, sulfo-, cyano- or nitro-substituted phenyl; or electron-withdrawing substituted phenylethyl. Most preferably, Y represents methyl, β-cyanoethyl, or 4-nitrophenylethyl.

The coupling reaction is conducted under standard conditions used for the synthesis of oligonucleotides and conventionally employed with automated oligonucleotide synthesizers. Such methodology will be known to those skilled in the art and is described in the pertinent texts and literature, e.g., in D. M. Matteuci et al. (1980) Tet. Lett. 521:719 and U.S. Pat. No. 4,500,707. The product of the coupling reaction may be represented as structural formula (IV), as follows:

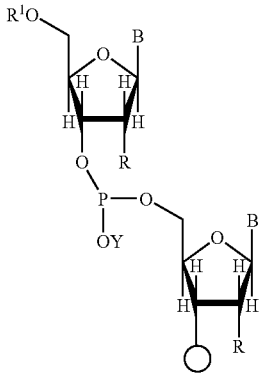

(IV)

In the second step of the synthesis, the product (IV) is treated with a combined oxidation/deprotection reagent in order oxidize the newly formed internucleoside linkage and to remove the hydroxyl protecting group at the 5' terminus, thus converting the moiety —OR¹ to —OH. Advantageously, this step may be conducted in connection with fluorescent or other readily detectable protecting groups, enabling monitoring of individual reaction steps. Further, the method is useful in carrying out either 3'-to-5' synthesis or 5'-to-3' synthesis. Finally, because of the far more precise chemistry enabled by the present invention, the method readily lends itself to the highly parallel, microscale synthesis of oligonucleotides.

The product of this concurrent oxidation and deprotection step may thus be represented as follows:

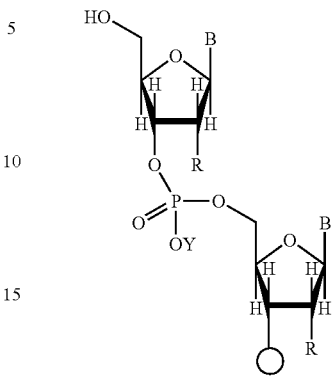

(VIII)

wherein B, R and Y are as defined earlier herein.

The combined oxidation/deprotection reagent may be selected to provide particularly advantageous synthesis conditions and characteristics, as are described herein. In a first embodiment, the combined oxidation/deprotection reagent provides for contacting of the elongating polynucleotide chain with an alpha effect nucleophile under neutral or mildly basic aqueous conditions to remove reactive site hydroxyl protecting groups where such protecting groups are labile under nucleophilic attack; the alpha effect nucleophile also serves to oxidize the phosphite triester linkage to the desired phosphotriester. In a separate embodiment, the combined oxidation/deprotection reagent provides for contacting of the elongating polynucleotide chain with an oxidizing agent in the presence of an acid under substantially non-aqueous conditions where the reactive site hydroxyl protecting group is an acid labile protecting group. The reagent will thus be selected based upon choice of protecting group and reaction conditions desired based upon whether aqueous or non-aqueous conditions are desired, whether acid catalyzed depurination of the product is a concern, or other considerations as will be apparent to the skilled practitioner given the disclosure herein.

In the first embodiment briefly discussed above, the combined oxidation/deprotection reagent provides a nucleophilic deprotection reagent under neutral or mildly basic conditions in aqueous solution. During the second step of the polynucleotide synthesis cycle (the oxidation/deprotection step in FIG. 2), the product (see formula (IV)) is treated with an "alpha effect" nucleophile in order to remove the protecting group at the reactive site hydroxyl (e.g. the 5' terminus), thus converting the moiety —OR1 to —OH. The alpha effect nucleophile also oxidizes the newly formed phosphite triester linkage (see formula (IV)) to give the desired phosphotriester linkage as shown in formula (VIII).

In a preferred embodiment, the nucleophilic deprotection reagent that exhibits an alpha effect is a peroxide or a mixture of peroxides. The pH at which the oxidation/deprotection reaction is conducted may generally range from one pH unit below the pKa of the nucleophilic deprotection reagent (that is, the pKa for formation of the corresponding peroxy anion) up to a pH of about 10.5. Preferably the pH will be within the range of the pKa of the nucleophilic deprotection reagent up to about 10. The peroxide may be either inorganic or organic. Suitable inorganic peroxides include those of the formula M+OOH−, where M is any counteranion, including for example H+, Li+, Na+, K+, Rb+, Cs+, or the like; and lithium peroxide or hydrogen peroxide can be particularly suitable. Suitable organic peroxides include those of the formula ROOH, where R is selected from the group consisting of alkyl, aryl, substituted alkyl and substituted aryl. More particularly, the organic peroxide will have one of the following three general structures (V), (VI) or (VII)

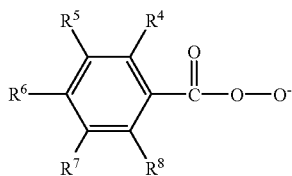

(V)

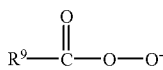

(VI)

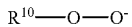

(VII)

in which R4 through R10 are generally hydrocarbyl optionally substituted with one or more nonhydrocarbyl substituents and optionally containing one or more nonhydrocarbyl linkages. Generally, R4 through R10 are independently selected from the group consisting of hydrido, alkyl, aryl, aralkyl, cycloalkyl, cycloalkylalkyl, alkenyl, cycloalkenyl, alkynyl aralkynyl, cycloalkynyl, substituted aralkyl, substituted cycloalkyl, substituted cycloalkylalkyl, substituted alkenyl, substituted cycloalkenyl, substituted alkynyl substituted aralkynyl, substituted cycloalkynyl; t-butyl-hydroperoxide or metachloroperoxybenzoic acid can be particularly suitable. As a specific example, the m-chloroperbenzoic acid (mCPBA) peroxy anion has been found to be useful for removal of protecting groups on the reactive site hydroxyl.

The use of a peroxy anion to effect concurrent removal of the non-carbonate protecting group and oxidation of the internucleoside linkage also removes, to a large extent, exocyclic amine-protecting groups such as acetyl, trifluoroacetyl, difluoroacetyl and trifluoroacetyl moieties. Thus, an added advantage herein is the elimination of a separate post-synthetic reaction step to remove exocyclic amine-protecting groups, as is required with conventional methods of synthesizing oligonucleotides. Elimination of this additional step significantly decreases the time and complexity involved in oligonucleotide synthesis.

An additional advantage of peroxy anions as deprotection reagents herein is that they may be readily activated or inactivated by simply changing pH. That is, the effectiveness of peroxides as nucleophiles is determined by their pKa. In buffered solutions having a pH significantly below the pKa of a particular peroxide, the peroxides are not ionized and thus are non-nucleophilic. To activate a peroxide and render it useful as a deprotection reagent for use herein, the pH is increased to near or above the pKa so that the peroxide is converted to a nucleophilic peroxy anion. Thus, one can carefully control the timing and extent of the deprotection reaction by varying the pH of the peroxide solution used.

Advantageously, this step is conducted in an aqueous solution at neutral pH or at a mildly basic pH, depending on the pKa of the nucleophilic deprotection reagent, such that acid-induced depurination is substantially avoided.

In the separate embodiment briefly discussed above, the combined oxidation/deprotection reagent provides an oxidizing agent in the presence of an acid under primarily non-aqueous conditions where the reactive site hydroxyl protecting group is an acid labile protecting group. Various oxidizing agents may be used in the solution, such as organic peroxides, oxaziridines or iodine. Preferably no more than 5% iodine, or even no more than 2% or 1% iodine is used, with less than 0.5% being most preferred. The combined oxidation/deprotection reagent may be a solution with a solvent which is primarily (that is, greater than 50%) non aqueous. Preferably, the combined oxidation/deprotection reagent has less than 20% or even less than 10% water, and may even be substantially anhydrous (that is, less than 5% water; however, less than 2%, 1% or 0.5% water may be present). The hydroxyl protecting group may be an acid labile protecting group, in which case the combined oxidation/deprotection reagent comprises an acid (including protic or Lewis acids such as zinc bromide) to deprotect the protected hydroxyl. Various acids may be used. For example, an acetic acid, such as a halogen substituted acetic acid (for example, di- or tri-chloracetic acid) may be used at a concentration, for example, of no more than 10% or no more than 6% (for example 5%), or even no more than 2% (for example, from 1% to any of 2% or 6% or 10%). Whichever acid is used, either it or some other composition component (for example, acetic acid or less preferably, water) should act as an oxygen donor so that the phosphite can be oxidized to the phosphate.

The nucleoside which is to be coupled (the "second nucleoside monomer") may particularly have a hydroxyl protected by an arylmethyl group (including mono-, di- or tri-phenyl methyl groups). The preferred acid labile protecting group is a dimethoxytrityl group, especially 4,4'-dimethoxytrityl. An acid labile protecting group on a hydroxyl may, for example, be at least 80% or 90% removed (or even at least 95% or 98% removed) in the acid solution used within 5 minutes (or even 2 minutes or 1 minute) at 20 EC. Additionally, the oxidation rate preferably exceeds the deprotection rate. For example, the oxidation may be sufficiently fast such that at least 50% (and preferably 70%, 80% or 90%) of phosphite to phosphate oxidation is complete by the time less than 20% (and preferably less than 10% or 5%) of deprotection has completed.

In the conventional synthesis method depicted schematically in FIG. 1, it is typical to use an aqueous solution of iodine for the oxidation step. However, phosphoramidite reagents that have been activated for coupling are highly reactive with water. The method of the current invention allows the option of reducing or substantially eliminating the presence of water during oxidation and deprotection. Thus, for example, in polynucleotide array synthesis, the current invention allows the number of wash steps (with non-aqueous solvent) over all of the addresses on the surface of the array to be reduced, with potential concomitant savings in time and solvents.

Different aspects of the present invention may be used to provide any one or more of a number of useful benefits. For example, with a decrease in the number of steps required, the time required to complete each cycle may be reduced. The number of solutions required for each cycle may also be reduced. The method could also be used to reduce or substantially eliminate the presence of water during oxidation. The need to use difficult to handle solvents such as pyridine or THF, may also be avoided.

Figure 2:
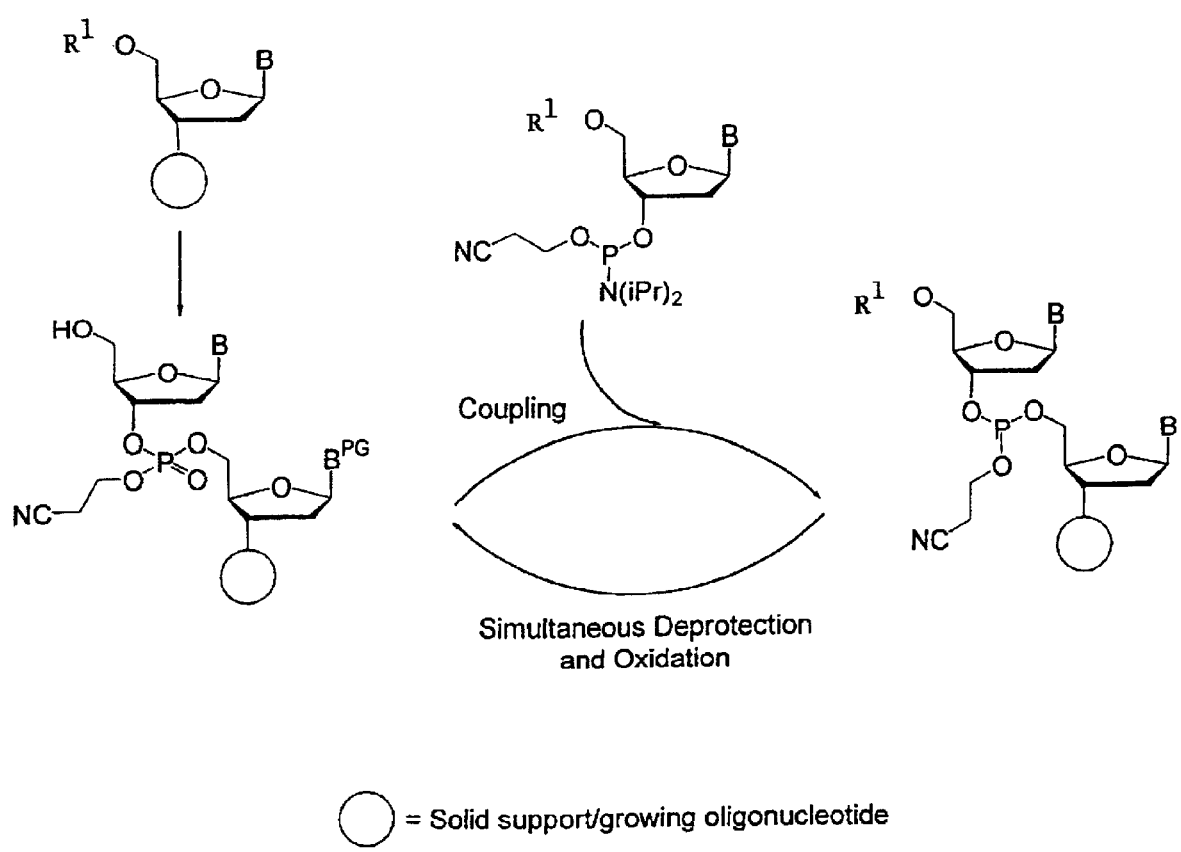
FIG. 2 schematically depicts an oligonucleotide synthesis method using phosphoramidite monomers and having a combined oxidation and deprotection step.

FIG. 2 schematically illustrates 3'-to-5' synthesis of an oligonucleotide using the method of the present invention. In the figure, the moiety $R^1$ represents a non-carbonate protecting group, as described above. As may be seen, deprotection and oxidation occur simultaneously. The synthesis may be contrasted with that schematically illustrated in FIG. 1, the prior, conventional method, where the conventional synthesis scheme entails separate oxidation and deprotection steps.

As explained earlier herein, the method of the invention also lends itself to synthesis in the 5'-to-3' direction. In such a case, the initial step of the synthetic process involves attachment of an initial nucleoside to a solid support at the 5' position, leaving the 3' position available for covalent binding of a subsequent monomer. The coupling reaction in which the nucleoside monomer becomes covalently attached to the 3' hydroxyl moiety of the support bound nucleoside is conducted under reaction conditions identical to those described for the 3'-to-5' synthesis. The coupling reaction is followed by treatment of the product with a combined oxidation/deprotection reagent in order oxidize the newly formed internucleoside linkage and to remove the hydroxyl protecting group at the 3' terminus, thus converting the moiety 3'-OR$^1$ to 3'-OH. The two-step process of coupling and deprotection/oxidation is repeated until the oligonucleotide having the desired sequence and length is obtained. Following synthesis, the oligonucleotide may, if desired, be cleaved from the solid support. The details of the synthesis in the 5'-to-3' direction will be readily apparent to the skilled practitioner based on the prior art and the disclosure contained herein.

The synthetic methods of the invention may be conducted on any solid substrate having a surface to which chemical entities may bind. Suitable solid supports are typically polymeric, and may have a variety of forms and compositions and derive from naturally occurring materials, naturally occurring materials that have been synthetically modified, or synthetic materials. Examples of suitable support materials include, but are not limited to, polysaccharides such as agarose (e.g., that available commercially as Sepharose®, from Pharmacia) and dextran (e.g., those available commercially under the tradenames Sephadex® and Sephacyl®, also from Pharmacia), polyacrylamides, polystyrenes, polyvinyl alcohols, copolymers of hydroxyethyl methacrylate and methyl methacrylate, silicas, teflons, glasses, and the like. The initial monomer of the oligonucleotide to be synthesized on the substrate surface is typically bound to a linking moiety which is in turn bound to a surface hydrophilic group, e.g., to a surface hydroxyl moiety present on a silica substrate.

Experimental:

The practice of the present invention will employ, unless otherwise indicated, conventional techniques of synthetic organic chemistry, biochemistry, molecular biology, and the like, which are within the skill of the art. Such techniques are explained fully in the literature.

The following examples are put forth so as to provide those of ordinary skill in the art with a complete disclosure and description of how to prepare and use the compounds disclosed and claimed herein. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric.

Figure 3:
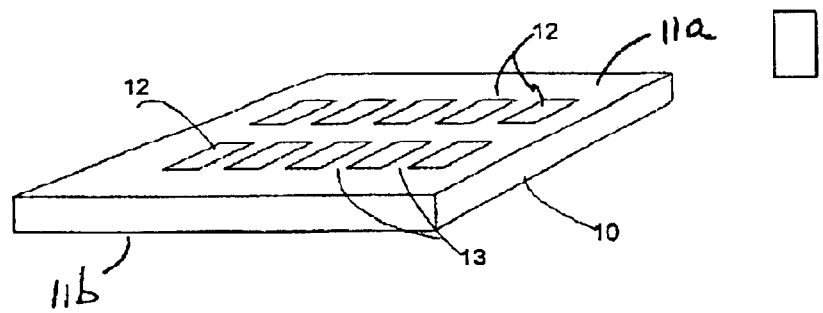
FIG. 3 is a perspective view of a substrate bearing multiple arrays, as may be produced by a method and apparatus of the present invention.
Figure 4:
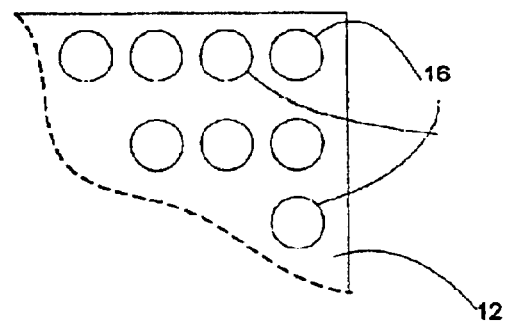
FIG. 4 is an enlarged view of a portion of FIG. 3 showing some of the identifiable individual regions (or "features") of a single array of FIG. 3.
Figure 5:
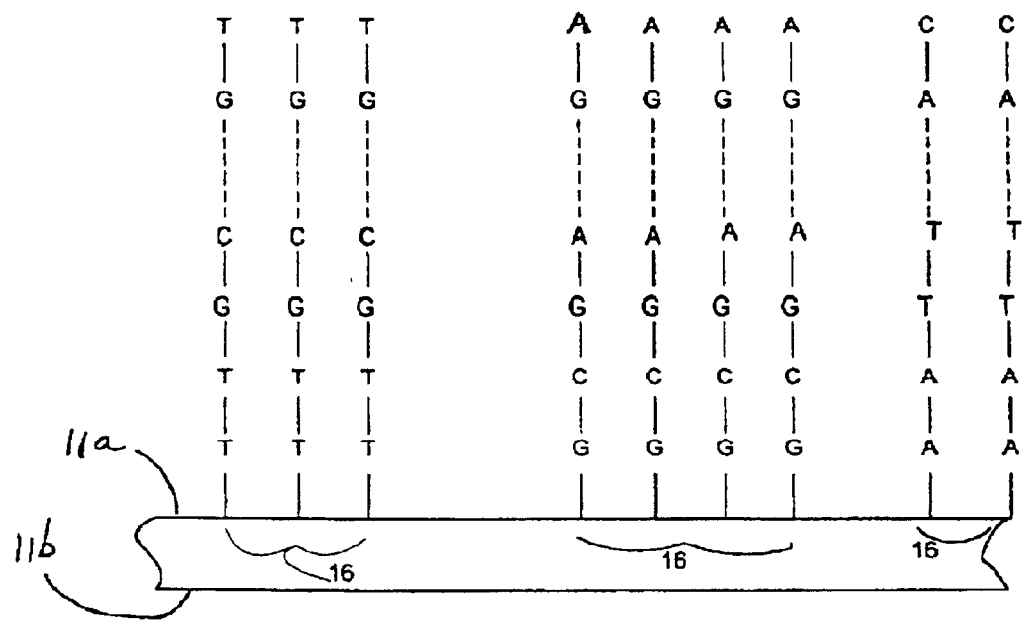
FIG. 5 is an enlarged cross-section of a portion of FIG. 4.

Referring now to FIGS. 3 through 5, the present invention may particularly be used to produce multiple identical arrays 12 (only some of which are shown in FIG. 3) across a complete front surface 11a of a single substrate 10 (which also has a back surface 11b). However, the arrays 12 produced on a given substrate need not be identical and some or all could be different. Each array 12 will contain multiple spots or features 16. The arrays 12 are shown as being separated by spaces 13. A typical array 12 may contain from 100 to 100,000 features. All of the features 16 may be different, or some or all could be the same. Each feature carries a predetermined polynucleotide having a particular sequence, or a predetermined mixture of polynucleotides. This is illustrated schematically in FIG. 5 where different regions 16 are shown as carrying different polynucleotide sequences. While arrays 12 are shown separated from one another by spaces 13, and the features 16 are separated from one another by spaces, such spaces in either instance are not essential.

In a typical execution of the present method, a polynucleotide is synthesized using one or more nucleoside phosphoramidites in one or more synthesis cycles having a) a coupling step, and b) a concurrent oxidation/deprotection step using the combined oxidation/deprotection reagent, as described above (with optional capping). In particular, the fabrication of each array 12 will be described. It will first be assumed that a substrate bound moiety is present at least at the location of each feature or region to be formed (that is, at each address). Such substrate bound moiety may, for example, be a nucleoside monomer which was deposited and deprotected at the location of each feature in a previous cycle, such that the deprotected reactive site hydroxyl is available for linking to another activated nucleoside monomer. Alternatively, the substrate bound moiety may be a suitable linking group previously attached to substrate 10. Both of these steps are known in in situ fabrication techniques. A droplet of a nucleoside phosphoramidite monomer solution is deposited onto the address and activated with a suitable activator (for example, a tetrazole, an imidazole, nitroimidazole, benzimidazole and similar nitrogen heterocyclic proton donors). In the case of phosphoramidites a non-protic low boiling point solvent could be used, for example, acetonitrile, dioxane, toluene, ethylacetate, acetone, tetrahydrofuran, and the like. Suitable activators for phosphoramidites are known and include tetrazole, S-ethyl tetrazole, dicyanoimidazole ("DCI"), or benzimidazolium triflate.

Any suitable droplet deposition technique, such as a pulse jet (for example, an inkjet head) may be used. The nucleoside phosphoramidite may particularly be of formula (II) with R1 being dimethoxytrityl with R2 being of formula (III) where Y is cyanoethyl, X is N(isopropyl)$_2$ (and in which the 2' position may or may not have a hydroxy or protected hydroxy group present). Alternatively, DMT-O— could be on the 3' carbon and the phosphoramidyl group on the 5' carbon, if it was desired to have the polynucleotide grow in the 5' to 3' direction. Other protecting groups may be used such as those disclosed herein and as those commonly known in the art. Conventional known reaction conditions may be used. The activated phosphoramidyl group will then couple the nucleoside monomer through a corresponding phosphite linkage with the substrate bound moiety (again, a linking group previously attached to substrate 10 or a deprotected nucleoside monomer deposited in a previous cycle). Note that the phosphite linkage corresponding to the foregoing particular phosphoramidite will be as in formula (IV) above. Particularly in the case of phosphoramidites, the reaction is complete very rapidly at room temperature of about 20° C. (for example, in one or two seconds).

At this point, a capping of substrate bound reactive site hydroxyls which failed to couple with a nucleoside compound may optionally be performed using known procedures.

The resulting compound can then be reacted with the combined oxidation/deprotection reagent composition. Such a composition should oxidize the phosphite linkage at a rate which is greater than the deprotection rate, as discussed above. For any particular proposed composition, oxidation rate can be evaluated by measuring the oxidation rate on phosphite coupled nucleosides using the same composition modified such that the phosphite is not destabilized. Deprotection rate can be measured with the proposed composition (optionally deleting the oxidizing agent) and the two rates compared. Examples of suitable compositions are listed below. In manufacture of a typical array, suitable times for exposure of the substrate to such solutions may range from about 10 to 60 seconds followed by washing with a non-aqueous solvent for about 10 to 60 seconds: Suitable solvents include aromatic solvents (such as benzene, xylene and particularly toluene) as well as chlorinated hydrocarbons (particularly chlorinated lower alkyl hydrocarbons such as dichloromethane).

The above steps can be repeated at each of many addresses on substrate 10 until the desired polynucleotide at each address has been synthesized. It will be understood however, that intermediate, washing and other steps may be required between cycles, as is well known in the art of synthesizing polynucleotides. Note though that since oxidation and deprotection are accomplished with a single composition, no washes are required between such steps. Furthermore, as water may optionally be substantially eliminated, the thorough washing to remove water prior to the coupling step in the next cycle is not required or may be reduced. The cycles may be repeated using different or the same biomonomers, at multiple regions over multiple cycles, as required to fabricate the desired array or arrays 12 on substrate 10. Note that oxidation and deprotection is preferably performed by exposing substrate 10 (in particular, the entire first surface 11a) to the single combined oxidation/deprotection reagent composition, for example, by flowing such a solution across first surface 11a. When all cycles to form the desired polynucleotide sequences at all addresses on the array have been completed, the substrate is dipped into a 1:1 solution of a 40% methylamine in water and 28% ammonia in water. This solution removes the protecting groups on the phosphate linkages and on the purine or pyrimidine base exocyclic amine functional groups. The arrays may then be removed from the solution and washed with water and are ready for use.

Particular examples of the method of the present invention are provided below.

EXAMPLE I

On an ABI 394 synthesizer, the deblocking solution (3% TCA in dichloromethane) is removed and replaced with the modified Solution I or II below, and a 1 µmole cycle is modified. After the wash following the capping step, the oxidation step is deleted. The next washes are also removed. After the delivery of dichloromethane (bottle#19), the solution in position #14 is delivered during 30 seconds. Then a 20 seconds wait is used, then the column is washed with acetonitrile (#18).

All other reagents are conventional. After synthesis on a 1 µmole CPG (Controlled Porous Glass) column, the DNA material is recovered in a 2 ml solution of ammonia/methylamine (1:1) at room temperature during 2 hours. 50 µl of this solution is evaporated with a speedvac concentrator and resuspended in water. The solution is injected in an Agilent HPLC using an ion exchange column from Dionex. Analysis of the peaks gives an estimated cycle yield as indicated below. No difference was observed between conventional and modified chemistry on all 4 nucleobases (A, C, G and T).

Solution 1 was 50 ml dichloroacetic acid/50 ml acetic acid/3 grams iodine/900 ml toluene. The solution is stirred overnight and then can be used immediately. Solution 2 was 50 ml DCA/50 ml acetic acid/40 g iodine/900 ml toluene. The solution is stirred overnight and then can be used immediately.

Various polynucleotides were synthesized using Solutions I or II in the above method. The synthesized polynucleotides and yields for each of Solutions I and II are indicated below:

Solution I:

| Yield | $T_{20}$ (SEQ ID NO: 1) | 98% |
|---|---|---|
| | $TC_{19}$ (SEQ ID NO: 2) | 97% |
| | $TA_{19}$ (SEQ ID NO: 3) | 96% |
| | $(TG)_{10}$ (SEQ ID NO: 4) | N/A |

Solution II:

| Yield | $TC_{19}$ (SEQ ID NO: 2) | 96% |
|---|---|---|
| | $TA_{19}$ (SEQ ID NO: 3) | 97% |
| | $(TG)_{10}$ (SEQ ID NO: 4) | 97% |
| | $T_{20}$ (SEQ ID NO: 1) | 98% |

EXAMPLE II

On a functionalized glass support, using a synthesizer such as in FIG. 4, the deblocking solution is replaced with a single deblocking, oxidizing Solution III according to the present invention. The regular oxidation solution is removed from the synthesizer. There is no dichloromethane wash before the deblocking-oxidation step.

A typical cycle would be:

Coupling

Capping

Wash with acetonitrile

Oxidation/Deprotection

Wash

Delivery and wait over the surface total 20 to 30 seconds, then the solution is quickly removed from the surface. After total synthesis of one sequence over the entire surface, the slide is dipped in a solution of ammonia/methylamine (1:1) at room temperature during 2 hours. The solution is recovered and evaporated with a speedvac concentrator. Then it is resuspended in water and injected in an HPLC. The results are analyzed as previously explained.

Solution III: 50 grams of trichloroacetic acid and 2 grams of iodine are added to 1 liter of toluene. The solution is stirred overnight and can be used immediately.

Using the above method Pro25G, which has the sequence: TAT CAT CGT AGC TGG TCA GTG TAT CC (SEQ ID NO: 5), was synthesized with a 97% yield (20 or 30 seconds exposure).

Further Examples

Further examples were performed using the same method as Example I (ABI synthesizer) or Example II (using a synthesizer such as in FIG. 4). The results are illustrated in the TABLE below. In the TABLE: "COMPOSITION" is the composition of the solution used for simultaneous deblock and oxidation; "Sequence" is the polynucleotide sequence synthesized; "Contact Time" is the total contact time of the COMPOSITION with the support; "ABI" is the method according to Example I above, while "Flood" is the method of Example II above. The compositions were made up of solvents representing the indicated percentage by volume (total volume of all liquids was 500 ml), with the iodine being additional (and thus each 5 grams of iodine represents about 1% of the solution by weight). The sequence for HCV25 is: TGA GGT GGT ATC TAG TGA GGG GAC A (SEQ ID NO: 6).

TABLE 1

| EG. # | COMPOSITION | | | | Sequence | Contact Time | Yield | Method |
|---|---|---|---|---|---|---|---|---|
| 1 | 90% toluene | 5% DCA | 5% AcOH | 20.0 g iodine | T20 (SEQ ID NO:1) | 30 sec | 96.22% | Flood |
| | | | | | | 30 sec | 95.00% | ABI |
| | | | | | | 40 sec | 98.00% | ABI |
| | | | | | | 50 sec | 97.96% | ABI |
| | | | | | T10 (SEQ ID NO:7) | 10 sec | 64.00% | ABI |
| | | | | | | 20 sec | 83.00% | ABI |
| | | | | | | 50 sec | 97.85% | ABI |
| | | | | | | 60 sec | 98.15% | ABI |
| | | | | | (TG)10 (SEQ ID NO:4) | 40 sec | 96.70% | ABI |
| | | | | | | 50 sec | 96.88% | ABI |
| | | | | | | 60 sec | 97.08% | ABI |
| | | | | | (TG)5 (SEQ ID NO:8) | 30 sec | 92.36% | Flood |
| | | | | | | 40 sec | 93.61% | ABI |
| | | | | | | 50 sec | 95.10% | ABI |
| | | | | | HCV25 (SEQ ID NO:6) | 60 sec | no results | ABI |
| 2 | 90% toluene | 5% DCA | 5% AcOH | 10.0 g iodine | T20 (SEQ ID NO:1) | 30 sec | 97.97% | ABI |
| | | | | | | 50 sec | 86.78% | Flood |
| 3 | 90% toluene | 5% DCA | 5% AcOH | 5.0 g iodine | T10 (SEQ ID NO:7) | 30 sec | 92.41% | ABI |
| | | | | | T20 (SEQ ID NO:1) | 30 sec | no results | Flood |
| | | | | | | 50 sec | 97.92% | ABI |
| | | | | | TA19 (SEQ ID NO:3) | 30 sec | no results | Flood |
| | | | | | | 50 sec | 97.53% | ABI |
| | | | | | TC19 (SEQ ID NO:2) | 50 sec | 97.31% | ABI |
| 4 | 90% toluene | 5% DCA | 5% AcOH | 3.0 g iodine | T20 (SEQ ID NO:1) | 30 sec | 91.72% | Flood |
| | | | | | | 40 sec | 94.23% | Flood |
| | | | | | | 50 sec | 98.00% | ABI |
| | | | | | TA19 (SEQ ID NO:3) | 40 sec | no results | Flood |
| | | | | | | 50 sec | 95.67% | ABI |
| | | | | | TC19 (SEQ ID NO:2) | 50 sec | 97.31% | ABI |
| 5 | 90% toluene | 5% DCA | 5% AcOH | 1.0 g iodine | T20 (SEQ ID NO:1) | 40 sec | 96.95% | ABI |
| | | | | | | 50 sec | 96.28% | Flood |
| 6 | 95% toluene | 2.5% DCA | 2.5% AcOH | 3.0 g iodine | T20 (SEQ ID NO:1) | 40 sec | 88.60% | ABI |
| | | | | | | 50 sec | 89.86% | Flood |
| A | 94% toluene | 1% TCA | 5% AcOH | 1.0 g iodine | T10C10 (SEQ ID NO:9) | 50 sec | 91.53% | Flood |
| B | 99% toluene | 1% TCA | 0% AcOH | 2.0 g Iodine | T10C10 (SEQ ID NO:9) | 50 sec | 97.60% | Flood |
| C | 95% toluene | 5% TCA | 0% AcOH | 1.0 g iodine | T10C10 (SEQ ID NO:9) | 50 sec | 92.46% | Flood |
| | | | | | Pro25G (SEQ ID NO:5) | 10 sec | 93.30% | Flood |
| | | | | | | 15 sec | 96.72% | Flood |
| | | | | | | 20 sec | 93.72% | Flood |
| | | | | | | 30 sec | 97.15% | Flood |
| | | | | (old solution used 1 week later) | | 30 sec | 94.18% | Flood |
| | | | | | | 30 sec | 80.00% | ABI |
| | | | | new solution | | 30 sec | 94.23% | Flood |
| D | 88% toluene | 5% TCA | 5% AcOH | 1.0 g iodine + 2% water | T10C10 (SEQ ID NO:9) | 50 sec | 97.37% | Flood |
| E | 97% toluene | 1% TCA | 0% AcOH | 1.0 g iodine + 2% water | T10C10 (SEQ ID NO:9) | 50 sec | 79.03% | Flood |
| F | 94% toluene | 1% TCA | 5% AcOH | 2.0 g Iodine | T10C10 (SEQ ID NO:9) | 50 sec | no results | |
| G | 99% toluene | 1% TCA | 0% AcOH | 1.0 g iodine | T10C10 (SEQ ID NO:9) | 50 sec | 94.78% | Flood |
| | | | | | Pro25G (SEQ ID NO:5) | 30 sec | 94.24% | Flood |
| | | | | | | 30 sec | 95.64% | Flood |

TABLE 1-continued

| EG. # | COMPOSITION | | | | Sequence | Contact Time | Yield | Method |
|---|---|---|---|---|---|---|---|---|
| H | 93% toluene | 5% TCA | 0% AcOH | 2.0 g Iodine + 2% water | T10C10 (SEQ ID NO:9) | 50 sec | 91.53% | Flood |
| I | 90% toluene | 5% TCA | 5% AcOH | 1.0 g iodine | T10C10 (SEQ ID NO:9) | 50 sec | 97.35% | Flood |
|   |   |   |   |   | Pro25G (SEQ ID NO:5) | 30 sec | 90.84% | Flood |
| J | 92% toluene | 1% TCA | 5% AcOH | 1.0 g iodine + 2% water | T10C10 (SEQ ID NO:9) | 50 sec | no results |   |
| K | 97% toluene | 1% TCA | 0% AcOH | 2.0 g Iodine + 2% water | T10C10 (SEQ ID NO:9) | 50 sec | 100.00% | Flood |
| L | 88% toluene | 5% TCA | 5% AcOH | 2.0 g Iodine + 2% water | T10C10 (SEQ ID NO:9) | 50 sec | 83.61% | Flood |
| M | 92% toluene | 1% TCA | 5% AcOH | 2.0 g Iodine + 2% water | T10C10 (SEQ ID NO:9) | 50 sec | no results | Flood |
| N | 90% toluene | 5% TCA | 5% AcOH | 2.0 g Iodine | T10C10 (SEQ ID NO:9) | 50 sec | 95.29% | Flood |
| O | 93% toluene | 5% TCA | 0% AcOH | 2.0 g Iodine | T10C10 (SEQ ID NO:9) | 50 sec | 94.61% | Flood |
| P | 95% toluene | 5% TCA | 0% AcOH | 2.0 g Iodine | T10C10 (SEQ ID NO:9) | 50 sec | 94.10% | Flood |
| Q | 95% toluene | 3% TCA | 0% AcOH | 2.0 g Iodine + 2% water | PRO25G (SEQ ID NO:5) | 30 sec | 85.38% | Flood |
|   |   |   |   |   |   | 40 sec | 90.94% | Flood |
|   |   |   |   |   |   | 50 sec | 100% | Flood |
| R | 92.5% toluene | 5% TCA | 2.5% AcOH | 1.0 g iodine | PRO25G (SEQ ID NO:5) | 20 sec | 97.08% | Flood |
|   |   |   |   |   |   | 40 sec | 97.37% | Flood |
| S | 95% toluene | 2.5% TCA | 2.5% AcOH | 1.0 g iodine | PRO25G (SEQ ID NO:5) | 30 sec | 94.56% | Flood |
| T | 92.5% toluene | 2.5% TCA | 5% AcOH | 1.0 g iodine | PRO25G (SEQ ID NO:5) | 20 sec | no results | Flood |
|   |   |   |   |   | PRO25G (SEQ ID NO:5) | 40 sec | 89.36% | Flood |
| U | 96.5% toluene | 1% TCA | 2.5% AcOH | 1.0 g iodine | PRO25G (SEQ ID NO:5) | 20 sec | no results | Flood |
|   |   |   |   |   |   | 40 sec | no results | Flood |
| V | 97.5% toluene | 2.5% TCA | 0% AcOH | 1.0 g iodine | PRO25G (SEQ ID NO:5) | 20 sec | 92.37% | Flood |
|   |   |   |   |   |   | 40 sec | no results | Flood |
| W | 95% toluene | 5% TCA | 0% AcOH | 1.0 g iodine | PRO25G (SEQ ID NO:5) | 30 sec | 91.93% | Flood |

EXAMPLE III

Concurrent Deprotection and Internucleotide Bond Oxidation (A) Oligonucleotide Synthesis on Controlled Pore Glass:

Oligonucleotides are synthesized on CPG using an automated DNA synthesizer (ABI model 380A). The synthesis cycle used for 5'-DMT protected nucleoside phosphoramidites (Cycle 1) is shown in Table 3. This cycle is initially modified for the use of a combined oxidation/deprotection protocol simply by substituting the alternative combined oxidation/deprotection reagent mixtures for the 3% TCA solution (Step 8, Table 3) and varying the exposure times.

For the synthesis of longer sequences using nucleoside phosphoramidites having 5'-non-carbonate protecting groups, it is necessary to separate the combined oxidation/deprotection reagent mixture into a two-component system (Table 2), where the two components are preferably quickly mixed together shortly before use of the combined oxidation/deprotection reagent mixture. The separation of the combined oxidation/deprotection reagent mixture is accomplished using the capping ports on the synthesizer, and thus necessitates elimination of the capping step from the synthesis cycle. Table 3 shows the cycle for synthesis using nucleoside phosphoramidites having a 5' non-carbonate protecting group (Cycle 2):

TABLE 2

TWO-COMPONENT SYSTEM FOR STORAGE OF DEPROTECTION SOLUTION C

| | |
|---|---|
| Solution C-1 | 30% $H_2O_2$ (10 ml), LiOH (280 mg), dioxane (7.5 ml), 2.5 M Tris-Base (15 ml), water (42.5 ml) |
| Solution C-2 | 50–60% mCPBA (1.78 g), dioxane (42.5 ml) |

TABLE 3

OLIGONUCLEOTIDE SYNTHESIS CYCLES

| Step # | Function | Reagent | Cycle 1 Time, sec. | Cycle 2 Time, sec. |
|---|---|---|---|---|
| 1 | Wash | Acetonitrile | 25 | 25 |
| 2 | Coupling | Amidite (0.15 M, 30 eq) Tetrazole (0.5 M, 120 eq) in Anhydrous Acetonitrile | 2 × 30 | 2 × 30 |
| 3 | Wash | Acetonitrile | 5 | 5 |
| 4 | Capping | N-Methylimidazole/2,6-Lutidine/ Acetic Anhydride/THF (1/1/1/2, vol/vol/vol/vol) | 40 | — |
| 5 | Oxidation | 0.1 M $I_2$ in THF/Lutidine/Water (80/40/2, vol/vol/vol) | 30 | — |
| 6 | Wash | Acetonitrile | 25 | — |
| 7 | Wash | Dichloromethane (Cycle 1) 1,4-Dioxane (Cycle 2) | 25 | 25 |
| 8 | Deblock | 3% TCA in $CH_2Cl_2$ (Cycle 1) 1:1 mix of Solution C-1 & Solution C-2 from Table 2 (Cycle 2) | 2 × 30 | 480 |
| 9 | Wash | Dichloromethane (Cycle 1) 1,4-Dioxane (Cycle 2) | 25 | 25 |

The oligonucleotides synthesized on the solid support are deprotected with concentrated ammonium hydroxide (55° C., 24 hr). The ammonium hydroxide solutions are then removed from the support and evaporated to dryness. The crude oligonucleotides are reconstituted in distilled water and stored at –20° C.

HPLC analysis was performed by ion-exchange HPLC (Nucleogen 60-7DEAE, 4 mm ID×125 mm). Oligonucleotides were eluted from the column with a LiCl gradient (0.0–0.7 M) in a water/acetonitrile (60/40, v/v) buffer containing sodium acetate (0.002 M, pH 6.0).

Decomposition of MCPBA in the presence of LiOH results in the deprotection mixture being effective for only a few hours. In order to synthesize longer sequences, it is necessary to separate the combined oxidation/deprotection reagent mixture into a two component system (Table 2). This is accomplished using the capping ports on the automated DNA synthesizer. Separating the LiOH from the mCPBA and mixing just prior to deprotection allows the reagents to remain effective for several days.

(B) Protected Phosphoramidite Synthesis

Synthesis of DeoxyNucleoside 5'-O-Silyl Protected 3'-O-(N,N-disopropylamino) cyanoethylphosphoramidite.

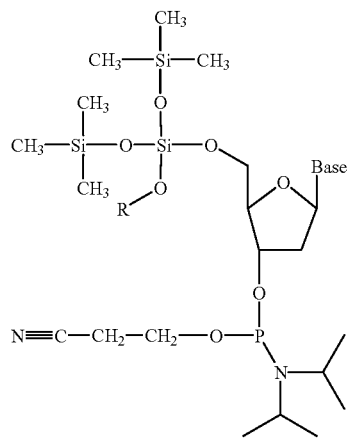

Various bis-(trimethylsiloxy) alkyoxychlorosilanes were prepared by the methods described by Scaringe and Caruthers U.S. Pat. No. 6,008,400 issued Dec. 28, 1999. The 2'-deoxynucleoside (12 mmol) was placed in a dry 200 ml round bottom flask containing a magnetic stirbar, fitted with a septum and placed under argon. The nucleoside was dissolved in anhydrous pyridine (50 mls) at room temperature. Once dissolved the solution was cooled to 0° C. in an ice/water bath. The bis-(trimethylsiloxy) alkyoxychlorosilane was added to the stirring solution drop-wise, with a syringe, over 30 minutes. Once the addition was complete, the ice/water bath was removed and the reaction was allowed to warm to room temperature. In order to completely dissolve any precipitate that was formed during addition of the silane, the magnetic stirrer was set to a vigorous stir rate. The reaction was allowed to stir at this rate for 1 hour at room temperature. The reaction was checked for completion by thin layer chromatography (TLC) using a solvent elution system of 60:40, ethyl acetate/hexanes. Once complete, the reaction was quenched by the addition of water (1 ml). The reaction mixture was evaporated to an oil on a rotary evaporator. Residual pyridine was removed from the oil by co-evaporation using toluene. The residual was redissolved in dichloromethane and extracted with an aqueous solution of sodium bicarbonate, followed by water and finally a saturated solution of sodium chloride. The dichloromethane layer was separated and dried over anhydrous sodium sulfate. The dichloromethane solution was concentrated on a rotary evaporator and placed on a silica column for medium pressure chromatography using a 50:50 mixture of ethyl acetate and hexanes as an eluent. Fractions from the column were collected and evaluated by TLC for the presence of the desired product. The products were obtained in a range of 40% to 70% yield.

The 3'-O-phosphoramidite products were produced using the 5'-O-silyl protected nucleosides, bis-(N,N-diisopropylamino) cyanoethyl phosphite and tetrazole. The protected nucleoside (2.0 mmol) was dissolved in 30 ml of anhydrous dichloromethane in a 100 ml dry round bottom flask fitted with a magnetic stirbar and a septum stopper. bis-(N,N-Diisopropylamino) cyanoethyl phosphite (2.5 mmol) and freshly sublimed tetrazole (0.4 mmol) were added to the stirring solution of the protected nucleoside. The reaction was placed under argon and allowed to stir at room temperature overnight. The reaction was quenched by the addition of 30 ml of saturated sodium bicarbonate. The dichloromethane layer was separated and dried over anhydrous sodium sulfate. The desired protected nucleoside phosphoramidite was isolated and purified on silica gel by medium pressure chromatography using a mixture of hexanes and ethyl acetate. The resulting phosphoramidite products were isolated in a range of 60% to 85% yield.

Synthesis of DeoxyNucleoside 5'-O-Ester Protected 3'-O-(N,N-disopropylamino) cyanoethylphosphoramidite.

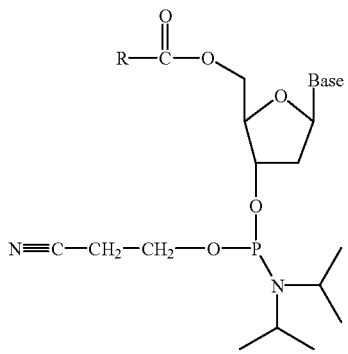

The 2'-deoxynucleoside (20.0 mmol) was desiccated by co-evaporation of water with anhydrous pyridine (3×100 mL). The anhydrous nucleoside was then re-dissolved in anhydrous pyridine (800 mL). The acid chloride or acid anhydride (22.0 mmol) was added dropwise to the pyridine solution with vigorous stirring. Care was taken to completely dissolve any precipitate formed during addition. After 2 hours, the reaction was checked for completion by thin layer chromatography (TLC) using a solvent elution system of 90:10, dichloromethane/methanol. Once complete, the reaction was quenched by the addition of water (2 ml). Solvent was removed from the reaction mixture under reduced pressure and residual pyridine was removed from the oily residue by co-evaporation with toluene (100 mL). The resulting oil was dissolved in dichloromethane (500 mL). The dichloromethane solution was extracted with saturated sodium bicarbonate (250 mL). The dichloromethane layer was separated then further extracted with brine (250 mL). The dichloromethane layer was finally separated, and dried over anhydrous sodium sulfate. The solvent was decanted, the sodium sulfate washed with three small volumes of dichloromethane. The dichloromethane solution was combined, and evaporated to yield a viscous yellow oil. The oil was redissolved in a minimum volume of dicholormethane and placed on a silica column for medium pressure chromatography using a 95:5 mixture of dichloromethane and methanol as an eluent. Fractions from the column were collected and evaluated by TLC for the presence of the desired product. The products were obtained in a range of 35% to 60% yield.

The 3'-O-phosphoramidite products were produced using the 5'-O-ester protected nucleosides, bis-(N,N-diisopropylamino) cyanoethyl phosphite and tetrazole. The protected nucleoside (2.0 mmol) was dissolved in 30 ml of anhydrous dichloromethane in a 100 ml dry round bottom flask fitted with a magnetic stirbar and a septum stopper. bis-(N,N-Diisopropylamino) cyanoethyl phosphite (2.5 mmol) and freshly sublimed tetrazole (0.4 mmol) were added to the stirring solution of the protected nucleoside. The reaction was placed under argon and allowed to stir at room temperature overnight. The reaction was quenched by the addition of 30 ml of saturated sodium bicarbonate. The dichloromethane layer was separated and dried over anhydrous sodium sulfate. The desired protected nucleoside phosphoramidite was isolated and purified on silica gel by medium pressure chromatography using ethyl acetate. The resulting phosphoramidite products were isolated in a range of 60% to 70% yield.

Synthesis of DeoxyNucleoside 5'-O-Carbamate Protected 3'-O-(N,N-disopropylamino) cyanoethylphosphoramidite.

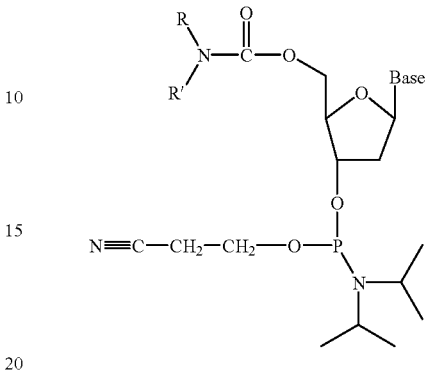

The 2'-deoxynucleoside (20.0 mmol) was desiccated by co-evaporation of water with anhydrous pyridine (3×100 mL). The anhydrous nucleoside was then re-dissolved in anhydrous pyridine (800 mL). The carbamoyl chloride (22.0 mmol) added dropwise to the pyridine solution with vigorous stirring. In some cases the carbamoyl chloride was a solid, which was dissolved in a minimum volume of anhydrous tetrahydrofuran prior to addition to the stirring solution of the nucleoside. After 2 hours, the reaction was checked for completion by thin layer chromatography (TLC) using a solvent elution system of 90:10, dichloromethane/methanol. Once complete, the reaction was quenched by the addition of water (2 ml). Solvent was removed from the reaction mixture under reduced pressure and residual pyridine was removed from the oily residue by co-evaporation with toluene (100 mL). The resulting oil was dissolved in dichloromethane (500 mL). The dichloromethane solution was extracted with saturated sodium bicarbonate (250 mL). The dichloromethane layer was separated then further extracted with brine (250 mL). The dichloromethane layer was finally separated, and dried over anhydrous sodium sulfate. The solvent was decanted, the sodium sulfate washed with three small volumes of dichloromethane. The dichloromethane solution was combined, and evaporated to yield a yellow oil. The oil was redissolved in a minimum volume of dicholormethane and placed on a silica column for medium pressure chromatography using a 95:5 mixture of dichloromethane and methanol as an eluent. Fractions from the column were collected and evaluated by TLC for the presence of the desired product. The products were obtained in a range of 25% to 50% yield.

The 3'-O-phosphoramidite products were produced using the 5'-O-ester protected nucleosides, bis-(N,N-diisopropylamino) cyanoethyl phosphite and tetrazole. The protected nucleoside (2.0 mmol) was dissolved in 30 ml of anhydrous dichloromethane in a 100 ml dry round bottom flask fitted with a magnetic stirbar and a septum stopper. bis-(N,N-Diisopropylamino) cyanoethyl phosphite (2.5 mmol) and freshly sublimed tetrazole (0.4 mmol) were added to the stirring solution of the protected nucleoside. The reaction was placed under argon and allowed to stir at room temperature overnight. The reaction was quenched by the addition of 30 ml of saturated sodium bicarbonate. The dichloromethane layer was separated and dried over anhydrous sodium sulfate. The desired protected nucleoside phosphoramidite was isolated and purified on silica gel by medium pressure chromatography using ethyl acetate. The resulting phosphoramidite products were isolated in a range of 60% to 80% yield.

Synthesis of DeoxyNucleoside 5'-O-Triphenylmethyl Protected 3'-O-(N,N-disopropylamino) cyanoethylphosphoramidite.

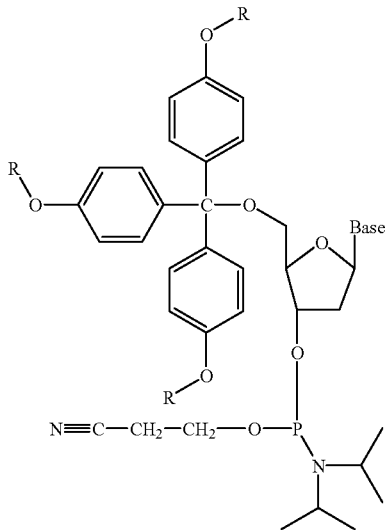

The protected tritylchlorides were prepared from rosolic acid and the corresponding phenol reactive protective compounds using the methods described by Sekine et al., *Bull. Chem. Soc. Jpn.*, 58, 336–339 (1985); *J. Org. Chem.*, 48, 3011–3014 (1983). The nucleosides or N-protected nucleosides were dissolved in anhydrous pyridine and the nucleosides made anhydrous by several repeated evaporations with anhydrous pyridine. The anhydrous nucleosides (10 mmol) were dissolved in anhydrous pyridine at a concentration of 0.1 M. The tritylchloride (12 mmol) was added to the stirring mixture of nucleoside and allowed to dissolve at room temperature. After dissolution, the reaction was allowed to stir for 2 hours. The extent of the reaction was evaluated by TLC using dichloromethane:methanol (95:5, vol:vol). If the reaction was shown not to be complete, a reaction catalyst such as N,N-dimethylaminopyridine was added and the reaction allowed to stir for another 2 hours. Once complete, the reaction was quenched by the addition of 1 ml of water and the pyridine removed under vacuum on a rotary evaporator. The residual was redissolved in 200 ml of dichloromethane and transferred to a separatory funnel. An equal volume of saturated sodium bicarbonate was added to the funnel and the organic layer extracted. The organic layer was separated bulk water removed by extraction with brine and dried over anhydrous sodium sulfate. The product was isolated and purified by medium pressure silica gel chromatography the product was eluted using a methanol gradient in dichloromethane. Fractions containing the product were collated and evaporated to dryness give a yield of 40 to 68%. The 3'-O-phosphoramidite products were produced using the 5'-O-trityl protected nucleosides, bis-(N,N-diisopropylamino) cyanoethyl phosphite and tetrazole. The protected nucleoside (2.0 mmol) was dissolved in 30 ml of anhydrous dichloromethane in a 100 ml dry round bottom flask fitted with a magnetic stirbar and a septum stopper. bis-(N,N-Diisopropylamino) cyanoethyl phosphite (2.5 mmol) and freshly sublimed tetrazole (0.4 mmol) were added to the stirring solution of the protected nucleoside. The reaction was placed under argon and allowed to stir at room temperature overnight. The reaction was quenched by the addition of 30 ml of saturated sodium bicarbonate. The dichloromethane layer was separated and dried over anhydrous sodium sulfate. The desired protected nucleoside phosphoramidite was isolated and purified on silica gel by medium pressure chromatography using ethyl acetate. The resulting phosphoramidite products were isolated in a range of 60% to 80% yield.

Figure 6:
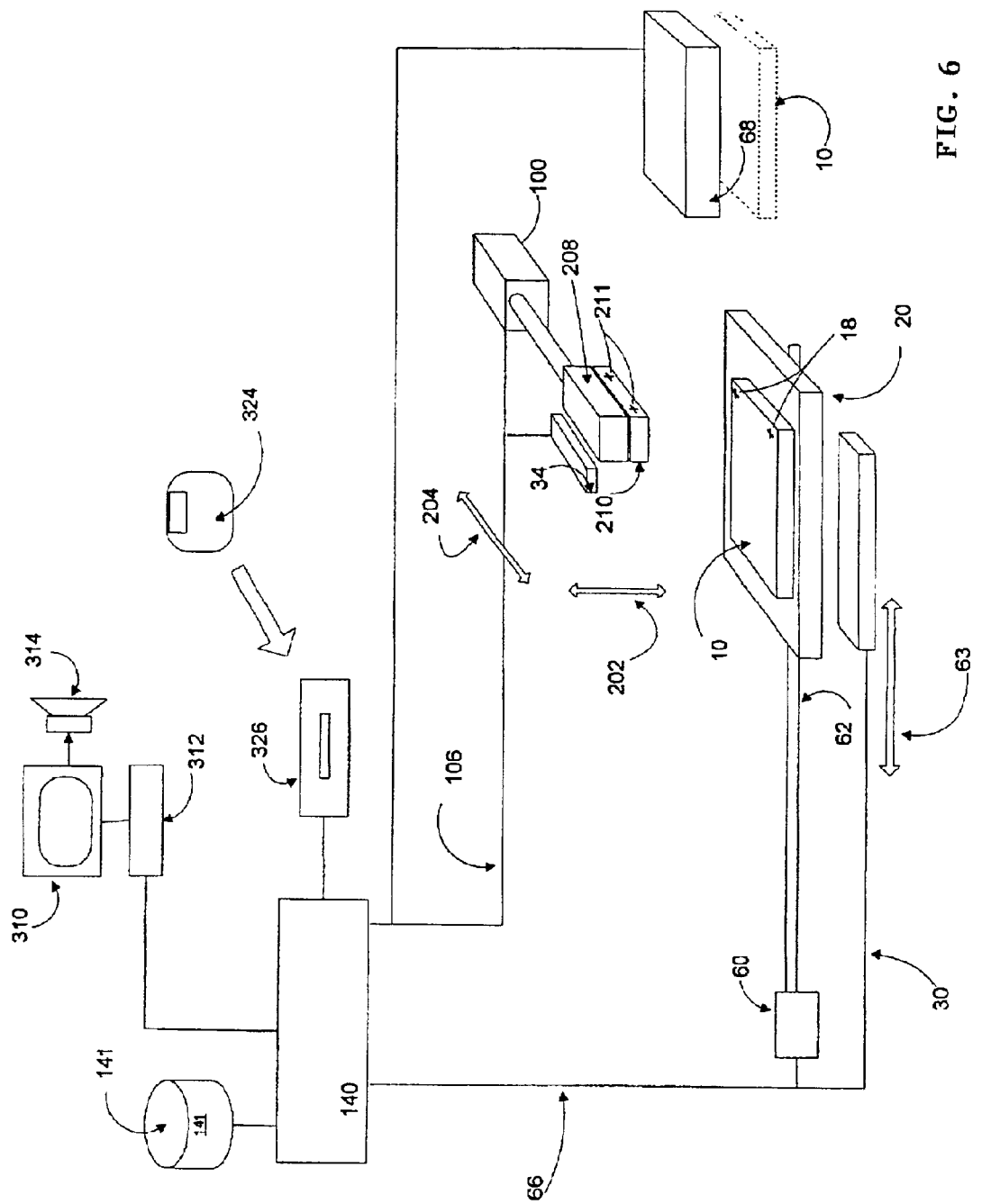
FIG. 6 is a schematic view of apparatus of the present invention.

Referring now to FIG. 6, a suitable apparatus for fabricating polynucleotide arrays in accordance with the present invention is shown. The apparatus shown includes a substrate station 20 on which can be mounted a substrate 10. Pins or similar means (not shown) can be provided on substrate station 20 by which to approximately align substrate 10 to a nominal position thereon. Substrate station 20 can include a vacuum chuck connected to a suitable vacuum source (not shown) to retain a substrate 10 without exerting too much pressure thereon, since substrate 10 is often made of glass. A flood station 68 is provided which can expose the entire surface of substrate 10, when positioned beneath station 68 as illustrated in broken lines in FIG. 6, to a fluid typically used in the in situ process, and to which all features must be exposed during each cycle (for example, the oxidation-deblock solutions of the above Examples, and wash buffer).

A dispensing head 210 is retained by a head retainer 208. The positioning system includes a carriage 62 connected to a first transporter 60 controlled by processor 140 through line 66, and a second transporter 100 controlled by processor 140 through line 106. Transporter 60 and carriage 62 are used execute one axis positioning of station 20 (and hence mounted substrate 10) facing the dispensing head 210, by moving it in the direction of arrow 63, while transporter 100 is used to provide adjustment of the position of head retainer 208 (and hence head 210) in a direction of axis 204. In this manner, head 210 can be scanned line by line, by scanning along a line over substrate 10 in the direction of axis 204 using transporter 100, while line by line movement of substrate 10 in a direction of axis 63 is provided by transporter 60. Transporter 60 can also move substrate holder 20 to position substrate 10 beneath flood station 68 (as illustrated in broken lines in FIG. 6). Head 210 may also optionally be moved in a vertical direction 202, by another suitable transporter (not shown). It will be appreciated that other scanning configurations could be used. It will also be appreciated that both transporters 60 and 100, or either one of them, with suitable construction, could be used to perform the foregoing scanning of head 210 with respect to substrate 10. Thus, when the present application recites "positioning" one element (such as head 210) in relation to another element (such as one of the stations 20 or substrate 10) it will be understood that any required moving can be accomplished by moving either element or a combination of both of them. The head 210, the positioning system, and processor 140 together act as the deposition system of the apparatus. An encoder 30 communicates with processor 140 to provide data on the exact location of substrate station 20 (and hence substrate 10 if positioned correctly on substrate station 20), while encoder 34 provides data on the exact location of holder 208 (and hence head 210 if positioned correctly on holder 208). Any suitable encoder, such as an optical encoder, may be used which provides data on linear position.

Head 210 may be of a type commonly used in an ink jet type of printer and may, for example, include five or more chambers (at least one for each of four nucleoside phosphoramidite monomers plus at least one for a solution of solid activator) each communicating with a corresponding set of multiple drop dispensing orifices and multiple ejectors which are positioned in the chambers opposite respective orifices. Each ejector is in the form of an electrical resistor operating as a heating element under control of processor 140 (although piezoelectric elements could be used instead). Each orifice with its associated ejector and portion of the chamber, defines a corresponding pulse jet. It will be appreciated that head 210 could, for example, have more or less pulse jets as desired (for example, at least ten or at least one hundred pulse jets). Application of a single electric pulse to an ejector will cause a droplet to be dispensed from a corresponding orifice. Certain elements of the head 210 can be adapted from parts of a commercially available thermal inkjet print head device available from Hewlett-Packard Co. as part no. HP51645A. Alternatively, multiple heads could be used instead of a single head 210, each being similar in construction to head 210 and being provided with respective transporters under control of processor 140 for independent movement. In this alternate configuration, each head may dispense a corresponding biomonomer (for example, one of four nucleoside phosphoramidites) or a solution of a solid activator.

As is well known in the ink jet print art, the amount of fluid that is expelled in a single activation event of a pulse jet, can be controlled by changing one or more of a number of parameters, including the orifice diameter, the orifice length (thickness of the orifice member at the orifice), the size of the deposition chamber, and the size of the heating element, among others. The amount of fluid that is expelled during a single activation event is generally in the range about 0.1 to 1000 pL, usually about 0.5 to 500 pL and more usually about 1.0 to 250 pL. A typical velocity at which the fluid is expelled from the chamber is more than about 1 m/s, usually more than about 10 m/s, and may be as great as about 20 m/s or greater. As will be appreciated, if the orifice is in motion with respect to the receiving surface at the time an ejector is activated, the actual site of deposition of the material will not be the location that is at the moment of activation in a line-of-sight relation to the orifice, but will be a location that is predictable for the given distances and velocities.

The apparatus can deposit droplets to provide features which may have widths (that is, diameter, for a round spot) in the range from a minimum of about 10 μm to a maximum of about 1.0 cm. In embodiments where very small spot sizes or feature sizes are desired, material can be deposited according to the invention in small spots whose width is in the range about 1.0 μm to 1.0 mm, usually about 5.0 μm to 500 μm, and more usually about 10 μm to 200 μm.

The apparatus further includes a display 310, speaker 314, and operator input device 312. Operator input device 312 may, for example, be a keyboard, mouse, or the like. Processor 140 has access to a memory 141, and controls print head 210 (specifically, the activation of the ejectors therein), operation of the positioning system, operation of each jet in print head 210, and operation display 310 and speaker 314. Memory 141 may be any suitable device in which processor 140 can store and retrieve data, such as magnetic, optical, or solid state storage devices (including magnetic or optical disks or tape or RAM, or any other suitable device, either fixed or portable). Processor 140 may include a general purpose digital microprocessor suitably programmed from a computer readable medium carrying necessary program code, to execute all of the steps required by the present invention, or any hardware or software combination which will perform those or equivalent steps. The programming can be provided remotely to processor 141, or previously saved in a computer program product such as memory 141 or some other portable or fixed computer readable storage medium using any of those devices mentioned below in connection with memory 141. For example, a magnetic or optical disk 324 may carry the programming, and can be read by disk reader 326.

Operation of the apparatus of FIG. 6 in accordance with a method of the present invention will now be described. First, it will be assumed that memory 141 holds a target drive pattern. This target drive pattern is the instructions for driving the apparatus components as required to form the target array (which includes target locations and dimension for each spot) on substrate 10 and includes, for example, movement commands to transporters 60 and 100 as well as firing commands for each of the pulse jets in head 210 coordinated with the movement of head 210 and substrate 10. This target drive pattern is based upon the target array pattern and can have either been input from an appropriate source (such as input device 312, a portable magnetic or optical medium, or from a remote server, any of which communicate with processor 140), or may have been determined by processor 140 based upon an input target array pattern (using any of the appropriate sources previously mentioned) and the previously known nominal operating parameters of the apparatus. The target drive pattern further includes instructions to head 210 and the positioning system of the apparatus to deposit the solution of solid activator at each region at which a biomonomer is to be deposited, separate from and preceding deposition of the biomonomer. Further, it will be assumed that each of four chambers of head 210 has been loaded with four different nucleoside phosphoramidite monomers, while a fifth chamber has been loaded with activating agent. It will also be assumed that flood station 68 has been loaded with all necessary solutions. Operation of the following sequences are controlled by processor 140, following initial operator activation, unless a contrary indication appears.

For any given substrate 10, the operation is basically as follows, assuming in situ preparation of a typical oligonucleotide using standard nucleoside phosphoramidite monomers as the biomonomers. A substrate 10 is loaded onto substrate station 20 either manually by an operator, or optionally by a suitable automated driver (not shown) controlled, for example, by processor 140. A target drive pattern necessary to obtain a target array pattern, is determined by processor 140 (if not already provided), based on nominal operating parameters of the apparatus. The apparatus is then operated as follows: (a) dispense appropriate next nucleoside phosphoramidite onto each region such that the first linking group is activated by solid activator and links to previously deposited deprotected nucleoside monomer; (b) move substrate 10 to flood station 68 for exposure to single combined oxidation/deprotection reagent composition as described herein, and washing solution, as well as optional capping solution, all over entire substrate as required; and (e) repeat foregoing cycle for all the regions of all desired arrays 12 until the desired arrays are completed (note that the biomonomer deposited and linked to the substrate bound moiety in one cycle becomes the substrate bound moiety for the next cycle). The phosphoramidite solution may include an activator, or alternatively a separate solid activator may be formed in the manner described in U.S. patent application Ser. No. 09/356,249, filed Jul. 16, 1999 and entitled "Biopolymer Arrays And Their Fabrication", incorporated herein by reference.

Note that during the above operation, pressure within head 210 can be controlled as described in co-pending patent applications "FABRICATING BIOPOLYMER ARRAYS", by Caren et al., Ser. No. 09/302,922, and "PREPARATION OF BIOPOLYMER ARRAYS" by A. Schleifer et al., Ser. No. 09/302,899, now U.S. Pat. No. 6,242,266, both filed Apr. 30, 1999 and both assigned to the same assignee as the present application, and the references cited therein. Processor 140 can execute the control of pressure within head 210.

With regard to the actual deposition sequence of biomonomer or activator solution droplets, as already mentioned, in this sequence processor 140 will operate the apparatus according to the target drive pattern, by causing the positioning system to position head 210 facing substrate station 20, and particularly the mounted substrate 10, and with head 210 at an appropriate distance from substrate 10. Processor 140 then causes the positioning system to scan head 210 across substrate 14 line by line (or in some other desired pattern), while co-ordinating activation of the ejectors in head 210 so as to dispense droplets in accordance with the target pattern. This can be continued until all arrays 12 to be formed on substrate 10 have been completed. The number of spots in any one array 12 can, for example, be at least ten, at least one hundred, at least one thousand, or even at least one hundred thousand.

At this point the droplet dispensing sequence is complete.

Arrays fabricated by methods and apparatus of the present invention, can be used to evaluate for the presence of one or more target polynucleotides in a known manner. Basically, this involves exposing the sample, normally as a fluid composition, to the array, such that target polynucleotide which may be present will bind to one or more predetermined regions of the array. The binding pattern on the array may then be observed by any method (such as by observing a fluorescence pattern), and the presence of the target evaluated based, in whole or in part, on the observed binding pattern.

Modifications in the particular embodiments described above are, of course, possible. For example, where a pattern of arrays is desired, any of a variety of geometries may be constructed other than the organized rows and columns of arrays 12 of FIG. 3. For example, arrays 12 can be arranged in a series of curvilinear rows across the substrate surface (for example, a series of concentric circles or semi-circles of spots), and the like. Similarly, the pattern of regions 16 may be varied from the organized rows and columns of spots in FIG. 2 to include, for example, a series of curvilinear rows across the substrate surface(for example, a series of concentric circles or semi-circles of spots), and the like. Even irregular arrangements of the arrays or the regions within them can be used, at least when some means is provided such that during their use the locations of regions of particular characteristics can be determined (for example, a map of the regions is provided to the end user with the array).

The present methods and apparatus may be used to form arrays of polynucleotides or other polymers made of monomers having a hydroxy protecting group and which are initially linked through a phosphite group (which is then oxidized) on surfaces of any of a variety of different substrates, including both flexible and rigid substrates. Preferred materials provide physical support for the deposited material and endure the conditions of the deposition process and of any subsequent treatment or handling or processing that may be encountered in the use of the particular array. The array substrate may take any of a variety of configurations ranging from simple to complex. Thus, the substrate could have generally planar form, as for example a slide or plate configuration, such as a rectangular or square or disc.

In many embodiments, the substrate will be shaped generally as a rectangular solid, having any desired dimensions, such as a length in the range about 4 mm to 500 mm; a width in the range about 4 mm to 500 mm. However, larger substrates can be used, particularly when such are cut after fabrication into smaller size substrates carrying a smaller total number of arrays 12. Substrates of other configurations and equivalent areas can be chosen. The configuration of the array may be selected according to manufacturing, handling, and use considerations.

The substrates may be fabricated from any of a variety of materials. In certain embodiments, such as for example where production of binding pair arrays for use in research and related applications is desired, the materials from which the substrate may be fabricated should ideally exhibit a low level of non-specific binding during hybridization events. In many situations, it will also be preferable to employ a material that is transparent to visible and/or UV light. For flexible substrates, materials of interest include: nylon, both modified and unmodified, nitrocellulose, polypropylene, and the like, where a nylon membrane, as well as derivatives thereof, may be particularly useful in this embodiment. For rigid substrates, specific materials of interest include: glass; fused silica, silicon, plastics (for example, polytetrafluoroethylene, polypropylene, polystyrene, polycarbonate, and blends thereof, and the like); metals (for example, gold, platinum, and the like).

The substrate surface onto which the polynucleotide compositions or other moieties are deposited may be smooth or substantially planar, or have irregularities, such as depressions or elevations. The surface may be modified with one or more different layers of compounds that serve to modify the properties of the surface in a desirable manner. Such modification layers, when present, will generally range in thickness from a monomolecular thickness to about 1 mm, usually from a monomolecular thickness to about 0.1 mm and more usually from a monomolecular thickness to about 0.001 mm. Modification layers of interest include: inorganic and organic layers such as metals, metal oxides, polymers, small organic molecules and the like. Polymeric layers of interest include layers of: peptides, proteins, polynucleic acids or mimetics thereof (for example, peptide nucleic acids and the like); polysaccharides, phospholipids, polyurethanes, polyesters, polycarbonates, polyureas, polyamides, polyethyleneamines, polyarylene sulfides, polysiloxanes, polyimides, polyacetates, and the like, where the polymers may be hetero- or homopolymeric, and may or may not have separate functional moieties attached thereto (for example, conjugated), While the foregoing embodiments of the invention have been set forth in considerable detail for the purpose of making a complete disclosure of the invention, it will be apparent to those of skill in the art that numerous changes may be made in such details without departing from the spirit and the principles of the invention. Accordingly, the invention should be limited only by the following claims.

All patents, patent applications, and publications mentioned herein are hereby incorporated by reference in their entireties.

What is claimed is:

1. A method of synthesizing a polynucleotide, comprising:
   (a) coupling a second nucleoside to a first nucleoside through a phosphite linkage,
   wherein the second nucleoside has a non-carbonate protecting group protecting a hydroxyl; and
   (b) exposing the product of step (a) to a composition which concurrently oxidizes the phosphite formed in step (a) to a phosphate and deprotects the protected hydroxyl of the second nucleoside.

2. A method according to claim 1 wherein the second nucleoside is a phosphoramidite and wherein steps (a) and (b) are repeated and the hydroxyl deprotected in a first iteration of step (b) reacts to form the phosphite linkage with the second nucleoside in the next iteration of step (a).

3. A method according to claim 1 wherein the non-carbonate protecting group is an acid labile protecting group and the composition comprises an acid to remove the non-carbonate protecting group.

4. A method according to claim 1 wherein the composition comprises a solution with a solvent which is primarily non-aqueous.

5. A method according to claim 4 wherein the solution is anhydrous.

6. A method according to claim 2 wherein the solution comprises iodine, an oxaziridine or a peroxide as an oxidizing agent.

7. A method according to claim 2 wherein the composition comprises an acetic acid and iodine, an oxaziridine, or an organic peroxide.

8. A method according to claim 1 wherein the non-carbonate protecting group is labile under nucleophilic attack under neutral or mildly basic conditions and the composition comprises a nucleophile that exhibits an alpha effect at neutral to mildly basic pH.

9. The method of claim 8 wherein the nucleophile is an inorganic peroxide of the formula M+OOH−, wherein M+ is a counterion selected from the group consisting of H+, Li+, Na+, K+, Rb+ and Cs+.

10. The method of claim 8, wherein the nucleophile is an organic peroxide of the formula (V), (VI) or (VII),

TABLE 5

| PHAGE | HPT1  | BSA   | HPT/BSA |
|-------|-------|-------|---------|
| HAX9  | 0.382 | 0.075 | 5       |
| HAX40 | 0.991 | 0.065 | 15      |
| HAX42 | 0.32  | 0.071 | 5       | in which R4 through R10 are hydrocarbyl optionally substituted with one or more nonhydrocarbyl substituents and optionally containing one or more nonhydrocarbyl linkages.

11. The method of claim 8 wherein the nucleophile is one of t-butyl hydroperoxide or m-chloroperoxybenzoic acid, or mixtures thereof.

* * * * *